United States Patent
Dudee

(10) Patent No.: US 11,833,029 B2
(45) Date of Patent: Dec. 5, 2023

(54) INTRAOCULAR OPTIC ASSEMBLY

(71) Applicant: Jitander Dudee, Lexington, KY (US)

(72) Inventor: Jitander Dudee, Lexington, KY (US)

(*) Notice: Subject to any disclaimer, the term of this patent is extended or adjusted under 35 U.S.C. 154(b) by 134 days.

(21) Appl. No.: 17/481,369

(22) Filed: Sep. 22, 2021

(65) Prior Publication Data
US 2022/0000608 A1    Jan. 6, 2022

Related U.S. Application Data

(63) Continuation of application No. 16/773,768, filed on Jan. 27, 2020, now Pat. No. 11,129,709.

(60) Provisional application No. 62/797,404, filed on Jan. 28, 2019.

(51) Int. Cl.
*A61F 2/16*    (2006.01)

(52) U.S. Cl.
CPC ............ *A61F 2/1635* (2013.01); *A61F 2/164* (2015.04); *A61F 2/1629* (2013.01); *A61F 2/1643* (2015.04)

(58) Field of Classification Search
CPC ...... A61F 2/1635; A61F 2/164; A61F 2/1643; A61F 2/1629
See application file for complete search history.

(56) References Cited

U.S. PATENT DOCUMENTS

| | | | |
|---|---|---|---|
| 2016/0184089 A1* | 6/2016 | Dudee | A61F 2/1648 623/6.22 |
| 2017/0258581 A1* | 9/2017 | Borja | A61F 2/1635 |
| 2018/0092738 A1* | 4/2018 | Tai | A61F 2/1613 |

* cited by examiner

*Primary Examiner* — Jerrah Edwards
*Assistant Examiner* — Aren Patel
(74) *Attorney, Agent, or Firm* — Black McCuskey

(57) ABSTRACT

A method of inserting an intraocular optic assembly having at least an optic and ring members that are interconnected to one another with a plurality of stanchions can include winding at least one of the structures relative to at least another one of the other structures about a central optic axis whereby at least some of the stanchions are drawn around an intermediate or middle ring member and in between the optic and an outer ring member. The method can also include folding, after the winding, the intraocular optic assembly in half while retaining the at least some of the plurality of stanchions in between the optic and the outer ring member. The method can also include inserting, after the folding, the intraocular optic assembly in an eye through a slit in a cornea of the eye.

5 Claims, 8 Drawing Sheets

INTRAOCULAR OPTIC ASSEMBLY

CROSS-REFERENCE TO RELATED APPLICATIONS

This application is a continuation of U.S. patent application Ser. No. 16/773,768 for an ACCOMMODATING INTRAOCULAR LENS ASSEMBLY, filed on 2020 Jan. 27, which will issue on 2021 Sep. 28 as U.S. Pat. No. 11,129,709, which is hereby incorporated by reference in its entirety. This application also claims the benefit of U.S. Pat. App. Ser. No. 62/797,404 for an ACCOMMODATING INTRAOCULAR LENS ASSEMBLY, filed on 2019 Jan. 28, which is hereby incorporated by reference in its entirety.

BACKGROUND

1. Field

The present disclosure relates to intraocular lenses having adjustable focus, such as found in Cooperative Patent Classification A61F 2/1629.

2. Description of Related Prior Art

U.S. Pat. No. 9,427,312 discloses an accommodating intraocular composite lens and related methods. The implantable intraocular lens and methods of manufacturing them provide a target degree of optical accommodation. In various embodiments, the lens includes at least one internal optic, an outer shell for enclosing at least a portion of the internal optic, and a fluid at least partially filling the outer shell.

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

SUMMARY

A method of inserting an accommodating intraocular lens assembly having at least an optic and ring members that are interconnected to one another with a plurality of stanchions can include winding at least one of the optic and the ring members about a central optic axis relative to at least another one of the two other structures whereby at least some of the plurality of stanchions are drawn around an intermediate ring member which is in between the optic and the other, outer ring member. The method can also include folding, after the winding, the accommodating intraocular lens assembly in half while retaining the at least some of the plurality of stanchions in between the optic and the outer ring member. The method can also include inserting, after the folding, the accommodating intraocular lens assembly in an eye through a slit in a cornea of the eye.

BRIEF DESCRIPTION OF THE DRAWINGS

The detailed description set forth below references the following drawings.

DETAILED DESCRIPTION

Figure 1:
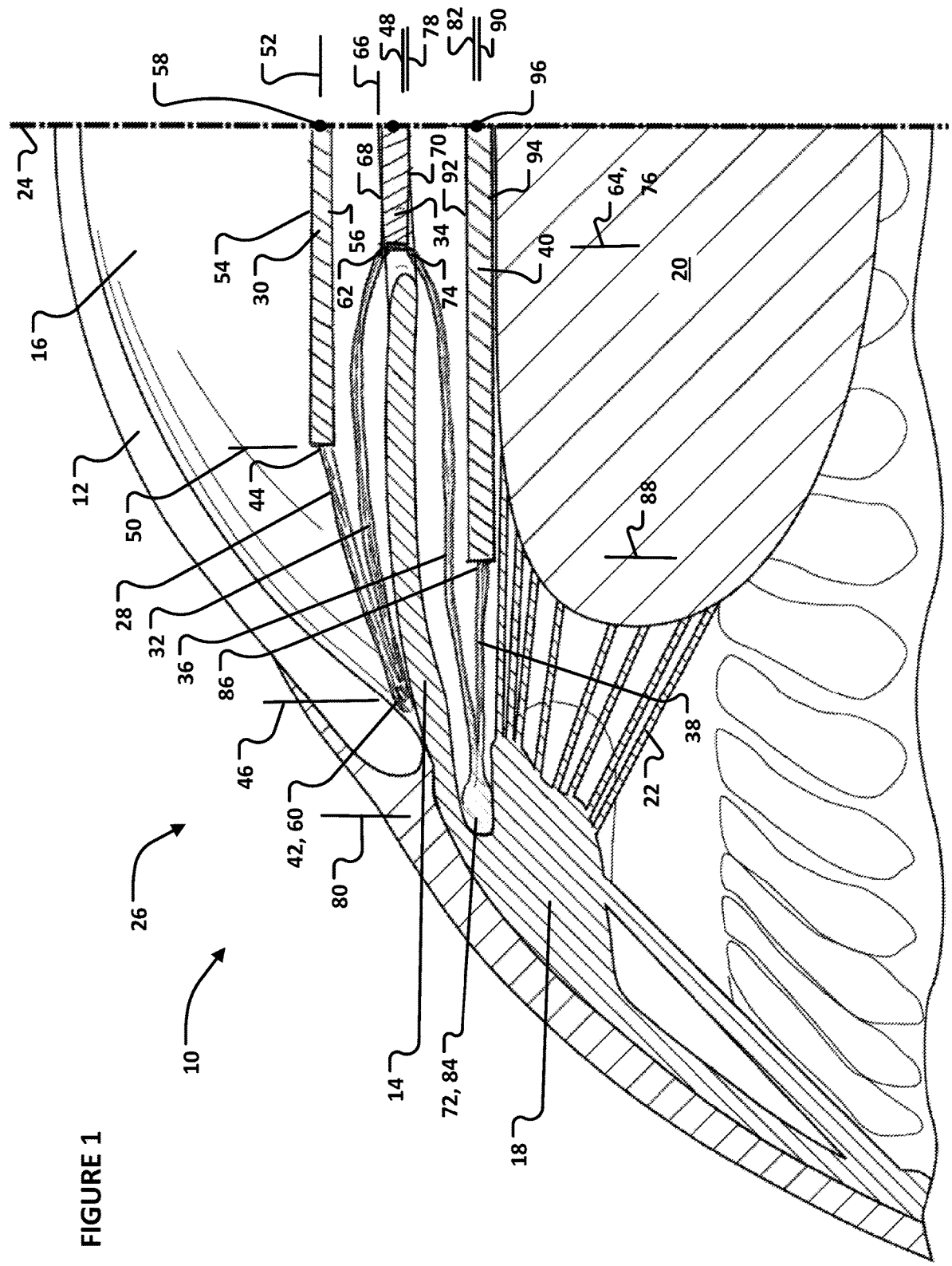
FIG. 1 is a cross-section of a first exemplary embodiment of the present disclosure positioned in an eye.

A plurality of different embodiments of the present disclosure is shown in the Figures of the application. Similar features are shown in the various embodiments of the present disclosure. Generally, similar features across different embodiments have been numbered with a common reference numeral and have been differentiated by an alphabetic suffix. Also, generally, similar features in a particular embodiment have been numbered with a common two-digit, base reference numeral and have been differentiated by a different leading numeral. Also, to enhance consistency, the structures in any particular drawing share the same alphabetic suffix even if a particular feature is shown in less than all embodiments. Similar features are structured similarly, operate similarly, and/or have the same function unless otherwise indicated by the drawings or this specification. Furthermore, particular features of one embodiment can replace corresponding features in another embodiment or can supplement other embodiments unless otherwise indicated by the drawings or this specification.

The following terms are useful in the defining the operating environment of one or more embodiments of the present disclosure:

Intraocular Lens or "IOL" or intraocular optic or IOL optic refers to a prosthetic optical lens placed within the eye to allow better visual functioning of the eye;

"Conventional IOL" refers to an IOL that has a single fixed focal point (also known as a monofocal IOL);

"Near Accommodation" or "Accommodation" refers to a change in the focal point of the optical system of the human eye from fixation on distant objects (those further away than about 6 meters from the eye) to near objects (those closer than about 0.5 meters from the eye), the term "accommodation" also includes the act of focusing on objects in the intermediate range of 6 to 0.5;

"Ciliary Body" or "CB" refers to the Ciliary Body of the eye including the various neuromuscular elements comprising the structure commonly referred to as the Ciliary Muscle, as well as the connective tissue joining the muscular elements and forming attachments of the ciliary muscle to the sclera and to the zonules or suspensory ligaments of the lens capsule. The muscular tissue within the CB is generally of the type known as "smooth muscle". Many microscopic muscle cells are connected to each other via elastic connective tissue forming bundles or rings of muscle that contract and stretch as a result of the combined contraction of the constituent muscle fibers;

"Ciliary Body accommodation" or "CBA" refers to the anatomical and physiological changes initiated by the act of voluntary human accommodation, during CB accommodation, impulses from the brain are transmitted to the nerves supplying the ocular tissues so that at least one eye is directed to align its optic axis towards the object of visual fixation, when at least one eye fixates on an object of visual interest, subconscious cues create an approximate estimate of the distance of the object from the eye and CB accommodation is triggered to the appropriate approximate extent required for the image from the object to be sharply focused on the retina, a process of reiterative biofeedback occurs so that the degree of CB accommodation is matched to the required working distance for sharp focus of the image from the object that is being viewed, other physiological actions are also linked to CB accommodation such as convergence (inwards rotation of eyes to triangulate and focus on a near object) and miosis (constriction of pupils to increase visual depth of field);

"Lenticular accommodation" refers to the alteration in optical power of the youthful or pre-presbyopic human eye in response to CB accommodation, the natural human lens is also known as the crystalline lens. It is enclosed within the lens capsule which in turn is connected to the ciliary body via many zonules (also known as suspensory ligaments) that attach close to the peripheral equator of the lens capsule on its posterior and anterior surfaces and extend in a radial fashion, suspending the crystalline lens from the CB. CB accommodation results in increased relative curvature of the front and rear lens capsule surfaces (also known collectively as the capsular bag), and a forward shift in the optical center of the crystalline lens, lenticular accommodation occurs as a result of decreased radial tension in the zonules because CB accommodation causes a relative anterior shift of the ring formed by the center of radial suspension the zonules, the cross sectional diameter of the eyeball is less at the relatively anterior location of the CB ring during CB accommodation, therefore the tension in the zonules is decreased allowing the elastic crystalline lens to revert to a shape that is more rounded in its anterior and posterior curvatures;

"Ciliary Sulcus" Refers to the ring like space bounded posteriorly by the ciliary process and suspensory ligaments of the lens (zonules) and bounded anteriorly by the posterior surface of the iris, the ciliary sulcus is bounded peripherally by the soft tissues overlying the ciliary body, these soft tissues separate the ciliary sulcus from the muscular components of the ciliary body, specifically the circular or annular portions of the ciliary muscle, the meridional portions of the ciliary muscle lie more peripherally and are anchored at the scleral spur, the ciliary sulcus extends for 360 degrees at the base of the iris, is vertically oval in humans and decreases in diameter during CBA;

"UBM" or "Ultrasound biomicroscopy" refers to imaging studies of the eye which show characteristic biometric changes that occur during ciliary body contraction, for understanding of the intended working of embodiments of this present disclosure, it is necessary to define some biometric features that change during CBA:

"SSD" (sulcus-to-sulcus diameter)—distance between opposite points in the ciliary sulcus, this will vary between individuals due to normal anatomic differences depending on the axial location of the opposite points because the ciliary sulcus is oval instead of circular in the near accommodated state in comparison to the relaxed state as CBA reduces SSD, "ICPA" (Iris-ciliary process angle)—the angle between the plane of the iris and the direction of the ciliary process from between which the lens zonules extend to the equator of the capsular bag, "ACA" (anterior chamber angle)—the angle between the plane of the peripheral iris and the inner layer of the cornea where they meet close to the iris root;

"Annular muscle contraction" or "AMC" refers to the morphological changes occurring during the contraction and relaxation of an annular or sphincteric muscle, specifically, it relates to the shape changes of the round portion of the ciliary muscle during CBA, the ring shaped "round" portion of the ciliary muscle encloses a central opening known as a lumen, which forms the external boundary of the ciliary sulcus, when an annular muscle contracts its total volume remains essentially unchanged but the circle surrounding the lumen in the plane of the lumen constricts, each point lining the lumen moves in relation to its neighbor during contraction and relaxation so that there are no two points that remain stationary relative to each other;

"Elastic biological surface" or "EBS" refers to a flexible membrane that forms the outside enclosure of an annular muscle or other elastic biological surface such as the capsule (or capsular bag) of the crystalline lens;

"Point-to-point contraction linking" or "PPCL" refers to the ability of a device to remain in contact with an elastic biological surface during the entire cycle of contraction and expansion without slipping at its contact points and without offering sufficient resistance to impede movement or cause damage by abrasion or penetration, for a device to be usefully coupled to an annular muscle (such as that found in the CB) it is essential for the device to offer in a predictable manner only as much resistance to movement as is necessary to convert the contraction of the muscle (in this case the contraction associated with CBA) into useful work (in this case IOL accommodation or "IOLA"), effective PPCL depends on critical design elements related to the points of contact of the device to the elastic biological surface, the features in point of contact design to achieve effective PPCL include:

distribution and location—Points of contact should be located around a center of movement that is also the center of movement of the elastic biological surface, number—The points of contact should be numerous enough to maintain stable attachment during motion and distribute resistance evenly across biological surface, at least eight contact points can be desirable for PPCL to a device within the lumen of an annular muscle, too many points of contact if large will limit movement by causing crowding and if small, may impede biological function by causing scarring, size—large contact points in contact with elastic biological surfaces such as the ciliary sulcus or capsular bag will present resistance against contraction or expansion of those surfaces, the continuous expansion and contraction of an annular muscle (even with its surrounding connective tissue) against an inelastic surface is likely to cause damage to biological tissues by abrasion and deposition of eroded tissues, contact points that are too small are likely to cause damage by perforation or penetration into biological tissue, profile—curved contact points offer a variable surface area and some degree of "rocking" during expansion and contraction which protects biological tissue and reduces scarring, multiple protrusions are vulnerable to becoming entangled during implantation, becoming damaged or causing damage to biological tissue;

"Haptic Vaulting" when used in relation to IOLs refers to forward or backward movement of IOL optic in the direction of the visual axis relative to the distal ends of its haptics, in prior art Haptic vaulting is envisioned as a mechanism for achieving IOLA in capsular bag fixated IOLs in response to decreasing diameter of the capsular bag which may vertically compress the haptic ends, Haptic Vaulting may occur surreptitiously in even prior art conventional or monofocal IOLs, depending on nature and placement of the haptics within a fibrosed or contracted capsular bag;

"Rigid Vaulting" when used in relation to IOLs refers to forward or backward movement of IOL optic in the direction of the visual axis relative to the optical nodal point of the eye in response to mechanical forces within the eye, specifically, this relates to movement of an IOL fixed within a capsular bag (IOL-capsule diaphragm) in response to movements of the entire capsular bag caused by:

contraction or relaxation of the zonules attached to the capsular bag secondary to ciliary muscle contraction,
variations in fluid pressure (from aqueous humor or vitreous humor) between the anterior and posterior surfaces of the IOL-capsule diaphragm,
gravitational shifting of IOL in response to changes in eye position (Rigid Vaulting is widely believed to occur surreptitiously in prior art conventional or monofocal IOLs, but to a variable and unpredictable extent and therefore cannot be relied on to provide useful degree of IOLA);

"Pseudo-accommodation" refers to the retention of some functional unaided near vision in combination with good distance vision following cataract extraction in patients who do not have IOLA, in patients who have a fixed focal length IOL implanted, whose power is set for clear distant vision, it is the ability of such patients to have better than expected (although still limited) near vision (without reading glasses), its existence is due to the following factors or fortuitous conditions:

"Pinhole effect"—increased depth of field caused by decreasing aperture of the pupil during CBA and in conditions of high illumination, this effect may be enhanced in some lenses whose central curvature is higher than peripheral so that when the peripheral cornea is curtained off by the constricting pupil, the overall focus of the lens because closer, relying on the pinhole effect has the disadvantage of reducing amount of light available to the eye and hence compromising the overall quality of vision, Aspheric optic property of the IOL (Lens has more than one major focal point). This may be intentional or serendipitous: Multifocal IOL design including pupil independent (diffractive lenses, aspheric curvatures) and pupil assisted (linked to pupillary constriction like the pinhole effect but accentuated by the IOL deliberately having a higher power in its central curvature, and Fortuitous/serendipitous optical effects presenting a secondary near image due to lens tilt (induced lenticular astigmatism) and corneal myopic astigmatism (Asymmetry of corneal curvature or tilting of the IOL can cause astigmatism, for example in which vertical lines far away, are seen better than horizontal lines, with the reverse holding try for near, since writing tends be composed of vertical and horizontal lines, people with just the right degree of astigmatism learn to decode the otherwise blurred near vision), and Limited accommodation due to IOL forward movement during CBA which may occur with any IOL implanted in elastic capsular bag with intact zonular attachments where the IOL-capsular bag complex moves forward during CBA increasing the effective power of the IOL and causing its focal point to move from distance to near, younger post cataract patients are often seen to have less need for reading glasses than expected when their (non-accommodating) IOLs have been selected for distant focus in both eyes, it is thought that the combination of a vigorous scarring response (causing the posterior capsule to bind firmly around the edge of the lens, and still strong ciliary muscles, allows the IOL to move forward in a way similar to the natural lens, this effect is usually not of sufficient extent to obviate the need for reading glasses;

"Monovision" refers to the illusion of good near and far vision obtained by implanting a monofocal IOL in one eye whose focal point is for distance and another monofocal IOL in the fellow eye whose focal point is for near. Monovision can also achieve a form of pseudo-accommodation so that when both eyes are used together, one provides good monocular distance vision and the other provides acceptable monocular near vision if the brain is able to adapt to this method of correction, this technique is often not well tolerated and causes reduction in stereoscopic vision, the patient is able to use each eye for its working distance (distance or near) although this does not represent true accommodation;

"IOL accommodation" or "IOLA" refers to a change in the optical focal point of an intraocular lens (hereafter IOL) from a sharp distant focus to a sharp near focus (and intermediate distances when the object of visual attention is in between) in an attempt to simulate is lenticular accommodation in response to CB accommodation, IOL accommodation is not equivalent to the IOL multifocality achieved by multifocal IOLs described immediately below;

"Multifocal IOL" or "MFIOL" refers to an IOL designed to have multiple simultaneous focal point, MFIOLs offer a degree of pseudo accommodation by having multiple focal powers or curvatures molded into a single IOL resulting in images of objects at more than one working distance becoming focused simultaneously on the retina, however, the simultaneous presentation of more than one image by the IOL causes degradation and compromise of each of the images as well as troublesome visual symptoms of halos, glare, ghost images collectively known as dysphotopsia, the providential persistence of pupillary miosis associated with CB accommodation can be utilized to preferentially select the central portion of the IOL curvature for near focusing and allow input from the peripheral lens curvature when CB accommodation is relaxed, and the pupil becomes relatively dilated, however, this type of "pinhole effect" also compromises overall quality of the images and multifocal IOLs in general have limited utility because CB accommodation does not result in true IOL accommodation, the increased range of focus depth of field presented by a static multifocal IOL is offset by lower image quality and visual aberrations, the eye and brain have to learn to ignore the images that are not useful for the current working distance and therefore there is compromise in overall vision quality and comfort;

"Haptic" refers to an arrangement of structural elements whose primary purpose is to hold, support, maintain and fixate one or more other distinct elements or device within the eye, where the device serves a biologically important function;

"Haptic Passenger" refers to a functionally important device supported by the haptic, examples of Haptic Passengers and their associated functions include an optical lens system, a reservoir, depot or container for a therapeutic substance or drug, a diagnostic instrument or sensor;

"IOL haptic" or refers to a structural element of an IOL designed to hold an IOL in place within the eye, such as a haptic whose haptic passenger is a lens;

"IOL optic" refers to the optically active component of the IOL having light transmitting refractive power, such as the haptic passenger for an IOL haptic;

"Capsular bag" or "bag" refers to the partially elastic biological membrane which normally contains the lentil shaped crystalline lens of the eye between a front surface (anterior capsule) and a back surface (posterior capsule) which join at the equator of the capsular bag from which equator the lens is suspended from and connected to the processes of the ciliary body by zonules (or suspensory ligaments of the lens), the capsular bag is opened during cataract surgery to remove the cataractous lens by making a roughly circular opening in its anterior capsule, the capsular bag has traditionally been the desired location in which to place an IOL after cataract extraction, the IOL is normally placed through the anterior capsular opening or "rhexis" so that its spring like supporting haptics rest in or close to the equator of the bag, suspending the optic of the IOL within and perpendicular to the visual axis;

"Capsulorhexis" or "rhexis" refers to the surgical opening made in the capsular bag and is a vital step in modern cataract surgery, it is necessary to access the cataract for removal and to insert an IOL if it is to be placed in the capsular bag, and the terms "rhexis" and "incision" are used interchangeably herein;

"Posterior capsular fibrosis" or "Posterior capsular opacification" (PCO) refers to the migration and proliferation of fibroblast inside and around the remnants of the capsular bag following cataract surgery, in addition to reducing vision, the scar tissue formed by these fibroblasts causes scarring and contracture of the capsular bag resulting in loss of its elastic properties, posterior capsular fibrosis occurs to at least some extent in the majority of patients following cataract despite various precautions commonly taken to reduce it, contracture of the capsular bag can cause tilt or displacement of an IOL in contact with the bag and will limit post-operative capsular bag movement in response to CBA, the severity of posterior capsular fibrosis is unpredictable but often warrants YAG laser capsulotomy after surgery to break open the capsule when it interferes with vision, the behavior of the capsular remnants following YAG laser capsulotomy is even more unpredictable, this means that any AIOL that relies on capsular bag contraction for functioning is unlikely to be successful because CBA cannot be reliably translated into IOLA by the post-surgical capsular bag;

"Accommodating IOL" or "AIOL" refers to a prosthetic lens or IOL that seeks to restore the function of lenticular accommodation (other than by pseudo-accommodation or monovision) in a patient whose crystalline lens has been removed;

"Simple lens" refers to the concave and convex cross sections depicted in optical drawings and ray diagrams shown commonly in physics textbooks, wherein the convex or concave surfaces enclose a medium whose refractive index is different to that of the media in front and behind the lens, although its front and rear surfaces are separated such a lens has a point (which can actually lie outside the body of the lens) known as the optical center of the lens whose location and optical properties can be described in an idealized fashion by "Thin Lens Theory", and in a more complex, and potentially more accurate fashion by "Thick Lens Theory", the power of such a lens is normally fixed and does not change because the lens is solid and static, the power of a particular simple lens can be made different to that of another by altering one or both of the front and rear curvatures or the refractive index of the medium behind and/or in front of the lens;

"Compound lens" refers to a lens composed of two or more simple lenses whose overall optical parameters can be varied by varying the power of each component lens, varying the separation between the optical centers of the component lenses, and varying other spatial relationship (such as tilt and alignment) between the optical centers or surfaces of the component lenses;

"Flexible lens" refers to a lens composed of an optical medium which is fluid or gel like in mechanical property, and of essentially constant volume, and whose volume is contained and bounded across at least part of its surface by an elastic or flexible membrane, the power of a flexible lens can be varied by shape change of the fluid or gel like medium when such shape changes result in variations in curvature of the flexible membrane when the membrane lies across the visual axis, variation in separation of the front and back surfaces, and variation in location of optical center of lens;

"Biological lens" refers to a lens with front and back surfaces whose body is composed of regions of varying refractive index without clear demarcation or interface between the zones, the regions may be distributed so that the gradient in refractive index varies perpendicular to its optic axis (refractive index changing from center to periphery in a concentric radial fashion) and/or varies in the line of the optic axis so that the refractive index is maximum at the front surface, back surface or center of the lens, variations of the power of a biological lens can be achieved by a spatial redistribution of the regions of high and low refractive indices and may be achieved by overall change in the shape of the lens when it is contained within a flexible membrane or redistribution of the optical centers of the regions of different refractive index without overall shape change of the external boundaries of the lens capsule, resulting in a shifting of the optical center of the lens;

"Neo-biological lens" refers to a lens composed of material whose refractive index can be varied be electronic or photo-chemical means either across the entire material of the lens, or selectively in certain regions; and "Higher Order Aberrations" or "HOA" relates to imperfections of focusing of a nature more complex than lower order optical aberrations such as spherical error and astigmatism, clinically important examples of HOA include spherical aberration, coma and trefoil, correction of HOA can improve visual quality and satisfaction following ocular surgery.

The exact nature and relative importance of various physiological mechanisms active in the human eye during the act of accommodation is controversial. The theory of Helmholtz appears to be the most favored. It is agreed that contractions of the ciliary body/muscle occur in response to neural signals from the brain when accommodation is voluntarily or reflexingly initiated. It is also agreed that in the youthful eye, this contraction causes several mechanical changes that result in the optical dioptric power of the lens system becoming more positive and so shifting the focal point of the lens closer to the person. The optical power change is thought to result from an anterior shift of the overall optical center of the lens closer to the cornea and an increase in curvature of the anterior and/or posterior refracting surfaces of the lens (necessitated by the requirement to maintain constant volume within the enclosing capsular bag) when the lentil shaped lens decreases in circumference at its attachment points (zonular fibers) in the plane roughly perpendicular to the visual axis.

In practice, other subtle changes may also contribute to a lesser extent such as constriction of the pupil to induce a pin-hole effect to increase depth of field—pseudo accommodation, shift of the constricted pupillary center away from the relaxed pupillary center to preferentially select a new optical line of site within the eye of different refractive power, and change in lens shape may cause shifting of relative position within the lens, of areas of differing pliability, elasticity and refractive index to cause a change in overall power.

For AIOL design a clear understanding of the anatomical changes occurring in the eye during CBA is desirable. In some species, CBA results in muscular activity that alters the curvature of the cornea or the length of the eyeball amongst other changes, but in humans, alterations of the shape and location of the crystalline lens appear to be the main mediators of accommodation.

When CBA is initiated in humans, at least three muscular sub systems within the ciliary body are activated. First, there is an annular or circular component—a sphincter muscle in the shape of a toroid in a plane approximately perpendicular to the visual axis, located internally to the scleral coat of the eye within the partially elastic parenchyma or connective tissue of the CB. This annular component contracts on accommodation so that the toroid becomes smaller in diameter and thicker in its cross section while the plane of the toroid moves closer to the front of the eye in the line of the visual axis. This contraction releases tension on the lens zonules and capsular bag, thereby causing forward movement of the optical center of the lens and a reduction in the equatorial diameter of the lens capsule.

Second, meridional or longitudinal components that run in approximately parallel to each other slight curve under the sclera connection their relatively stationary attachment on the sclera at one end to the pars plana of the ciliary body at the other end. The effect of contraction of these fibers is to pull the area of attachment of lens zonules anteriorly along the interior surface of the eyeball as it approaches the cornea. The anatomy of the anterior eyeball is such so that this movement results in release in tension of the lens zonules, especially those connecting to the front surface of the lens capsule so that the lens returns to a more rounded shape and its optical center moves forward. The annular fibers of the ciliary muscle lie in a ring separated from the sclera and eyeball by the longitudinal fibers so that the contraction of the longitudinal fibers mechanically facilitates the contraction of the annular components by occupying and increasing the space between the outer aspect of the ring muscles and the sclera.

Third, oblique fibers that run a semi-spiral course under the sclera of the eyeball. They likely act as slings to reduce forces that might inwardly detach the pars plana of the ciliary body and prevent wrinkling of the pars plana of the ciliary body during CBA.

Although the ciliary muscle is usually depicted in cross section, it is actually a complex 3-D structure that is fixed at its outside margin to the sclera of the eyeball and whose inside margin suspends the zonules which connect to the capsular bag. Different species have at least three types of muscle fibers within the ciliary muscle. The exact contribution of the various mechanisms linked to accommodation are not fully known but for the purpose of at least some embodiments of the present disclosure the important points are that when contracted during accommodation the ciliary muscle concentrates into a toroid which decreases in inside diameter, increases in cross sectional area, and moves forward in the plane perpendicular to visual axis with regards to the location of its center of volume.

Contraction of the ciliary muscle leads to changes in the three dimensional shape of the lens capsule as well as displacement of the optical center of the lens in relation to the overall optical center of the eye itself. This displacement alters the overall focal point of the eye allowing variability of focus from distance to near objects.

When accommodation is relaxed in the human eye, outward radial pull via tension in the suspensory ligaments (zonules) of the lens leads to an increase in the circular diameter of the space contained within the lens capsule in the plane approximately perpendicular to the visual axis and path of light from distant objects to the central retina of the eye. The act of accommodation causes the ciliary muscle of the eye to contract which releases tension in the suspensory lens ligaments resulting in reduced diameter of the lens in the visual plane and changes in the anterior and posterior surface curvatures of the lens as well as shifting of the optical center of the lens which result in increased convex dioptric power of the lens and consequently of the whole optical system of the eye allowing near objects to be focused on the retina.

The crystalline lens of the eye is normally flexible and is suspended within an elastic capsule. This capsule has to be penetrated to remove the cataractous lens.

The shape of the lens capsule and enclosed lens in its natural state depends on the interaction between the elastic nature of the capsule and also (a) the tension in the supporting zonules whose force and direction is varied by contraction of the ciliary muscle, (b) resistance and pressure from the vitreous humor against the posterior capsule surface, (c) forces on the anterior surface of the lens capsule from aqueous humor and iris, (d) gravity, and (e) resistance to deformity of the contents of the lens capsule, normally the crystalline lens.

One or more embodiments of the present disclosure utilize biometric changes occurring during CBA. The primary biometric changes utilized are reductions in the sulcus-to-sulcus diameter (SSD), the anterior chamber depth (ACD), the iris-ciliary process angle (ICPA), and the iris-zonula distance (IZD, or posterior chamber depth). Indirect or secondary biometric changes occurring during CBA that can be utilized in one or more embodiments of the present disclosure include reductions in the ciliary process-capsular bag distance (CP-CBD) decreases and the ciliary ring diameter (CRD).

Although there is considerable variability in the exact measured mean values for the various anatomical distance and angles compared in the relaxed and near accommodated state, this is not surprising given the normal anatomical variations between studied individuals as well as the variety of instruments and techniques used in different studies. Additionally, the resolution of the current technology is still sub optimal, as are agreements in precise location of landmarks. Because of the above-mentioned factors, comparison of the various studies shows a wide variability of the mean measured values in both the relaxed and near accommodated state, as well as large standard deviations in the mean difference values. This results in low confidence in the statistical significance of the mean differences in many of the studies. However, at least some embodiments of the present disclosure assume that there are some consistent and predictable variations in measured anatomical parameters during near accommodation including (a) a decrease in the SSD (sulcus-to-sulcus diameter) from approximately 11 mm to approximately 10.5 mm, (b) a decrease in the ICPA (Iris-ciliary process angle) from approximately 40 degrees to approximately 22 degrees, (c) a decrease in the ACA (anterior chamber angle) from approximately 32 degrees to approximately 28 degrees, (d) a decrease in the distance from the ciliary sulcus to the apex of the cornea caused by movement of the plane of the ciliary sulcus anteriorly along the visual axis, and (e) an increase in the diameter of the circular portion of the ciliary muscle. One or more embodiments of the present disclosure can use the above anatomical changes to mechanically link CBA to IOLA in a manner superior to the prior art.

Referring now to FIG. 1, an eye 10 includes a cornea 12, an iris 14, an anterior chamber 16 disposed between the cornea 12 and the iris 14, a ciliary muscle 18, a capsular bag 20, and zonules 22 extending between the ciliary muscle 18 and the capsular bag 20. The exemplary eye 10 is centered on a central optic axis 24.

Figure 2:
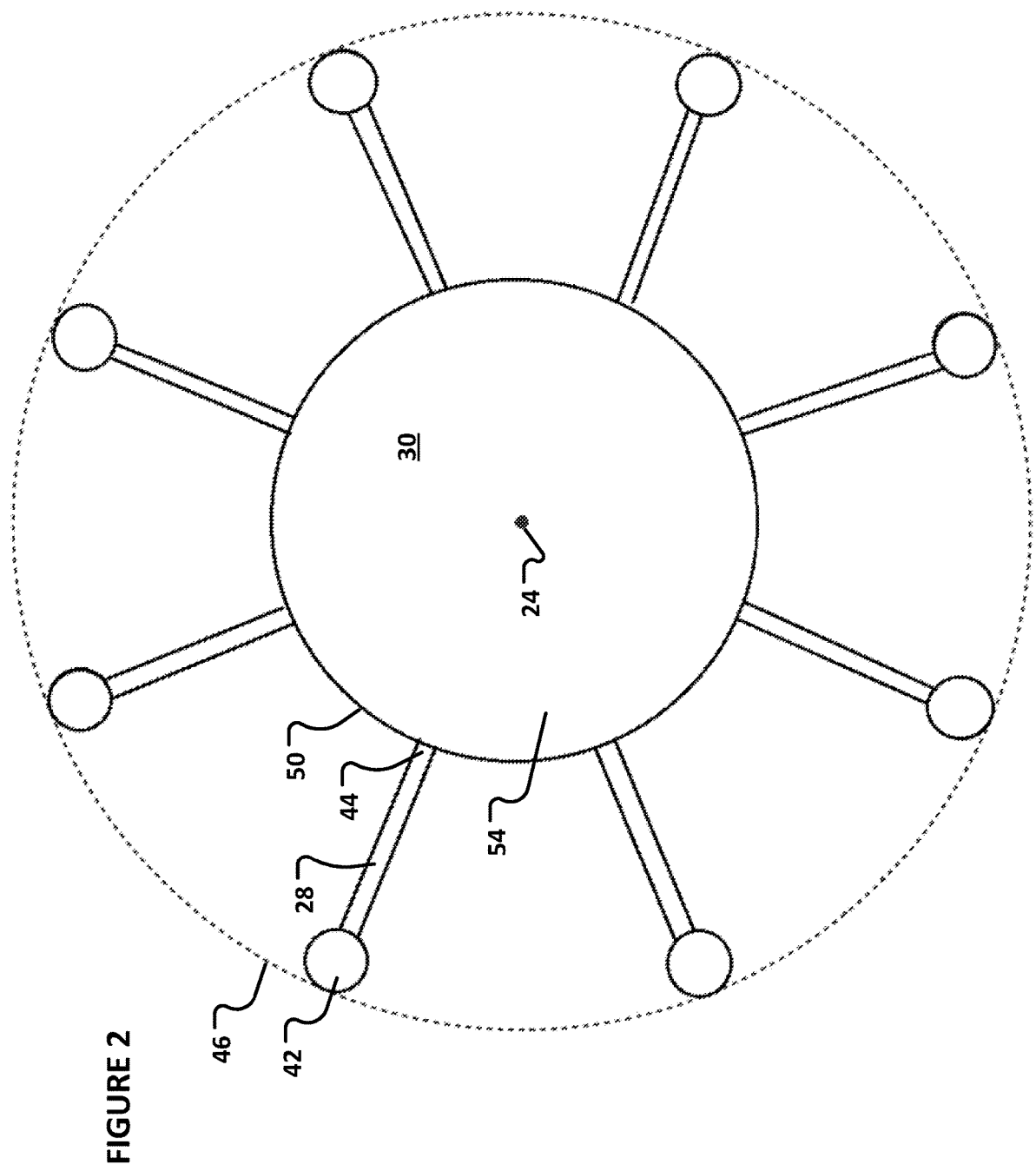
FIG. 2 is front view of the first exemplary embodiment of the present disclosure positioned in outside of the eye.

In one embodiment of the present disclosure, an accommodating intraocular lens assembly 26 can include a plurality of first stanchions 28, a forward optic 30, a plurality of second stanchions 32, an intermediate member 34, a plurality of third stanchions 36, a plurality of fourth stanchions 38, and an aft optic 40. The plurality of first stanchions 28 can each extend between a respective first base end 42 and a respective first distal end 44. As best shown in FIGS. 1 and 2, the plurality of first base ends 42 can be disposed in spaced relation to one another about a first arcuate periphery 46 in a first plane 48. The plurality of first distal ends 44 can be disposed in spaced relation to one another about a second arcuate periphery 50 in a second plane 52. The first arcuate periphery 46 can have a greater radius than the second arcuate periphery 50. The first arcuate periphery 46 and the second arcuate periphery 50 can be centered on the central optic axis 24. The first plane 48 and the second plane 52 can be spaced from one another along the central optic axis 24.

Referring again to FIG. 1, the forward optic 30 can have a first anterior side 54 and a first posterior side 56 and a first center 58 disposed between the first anterior side 54 and the first posterior side 56. The forward optic 30 can be connected with each of the plurality of first distal ends 44. The first center 58 of the forward optic 30 is moved along the central optic axis 24 in response to contraction of the first arcuate periphery 46.

The plurality of second stanchions 32 can each extend between a respective second base end 60 and a respective second distal end 62. The plurality of second base ends 60 can be disposed in spaced relation to one another about the first arcuate periphery 46 in the first plane 48. In this exemplary embodiment, the ends 42 and 60 are integral and bulbous. The plurality of second distal ends 62 can be disposed in spaced relation to one another about a third arcuate periphery 64 in a third plane 66. The first arcuate periphery 46 can have a greater radius than the third arcuate periphery 64. In the exemplary embodiment, the radius of the third arcuate periphery 64 is also less than the radius of the second arcuate periphery 50. The third arcuate periphery 64 can be centered on the central optic axis 24. The second plane 52 and the third plane 66 can be spaced from one another along the central optic axis 24.

The intermediate member 34 can have an anterior side 68 and a posterior side 70 and can be connected with each of the plurality of second distal ends 62. In the exemplary embodiment, the intermediate member 34 has a radially-outer perimeter that is circular and is disc-shaped, with a body defining the radially-outer perimeter that is circular and continuous within the radially-outer perimeter. In other words, the exemplary intermediate member 34 is a solid disc without apertures. In one or more embodiments of the present disclosure, the intermediate member 34 could include a sphero-cylindrical or aspheric lens.

The plurality of third stanchions 36 can each extend between a respective third base end 72 and a respective third distal end 74. The plurality of third base ends 72 can be disposed in spaced relation to one another about a fourth arcuate periphery 80 in a fourth plane 82. The plurality of third distal ends 74 can be disposed in spaced relation to one another about a fifth arcuate periphery 76 in a fifth plane 78. In the exemplary embodiment, the peripheries 64 and 76 have the same radius. The plurality of third distal ends 74 can be connected to the intermediate member 34. The fourth arcuate periphery 80 can have a greater radius than the fifth arcuate periphery 76. The fourth arcuate periphery 80 and the fifth arcuate periphery 76 can be centered on the central optic axis 24. The second plane 52 and the fifth plane 78 can be spaced from one another along the central optic axis 24.

The plurality of fourth stanchions 38 can each extend between a respective fourth base end 84 and a respective fourth distal end 86. The plurality of fourth base ends 84 can be disposed in spaced relation to one another about the fourth arcuate periphery 80 in the fourth plane 82. In this exemplary embodiment, the ends 72 and 84 are integral and bulbous. The plurality of fourth distal ends 86 can be disposed in spaced relation to one another about a sixth arcuate periphery 88 in a sixth plane 90. The fourth arcuate periphery 80 can have a greater radius than the sixth arcuate periphery 88. The sixth arcuate periphery 88 can be centered on the central optic axis 24. The second plane 52 and the sixth plane 90 can be spaced from one another along the central optic axis 24.

The aft optic 40 can have a second anterior side 92 and a second posterior side 94 and a second center 96 disposed between the second anterior side 92 and the second posterior side 94. The aft optic 40 can be connected with each of the plurality of fourth distal ends 86 whereby the second center 96 of the aft optic 40 is moved along the central optic axis 24 in response to contraction of the fourth arcuate periphery 80. In the exemplary embodiment, the aft optic 40 is positioned posteriorly of the forward optic 30 and is a positive-power lens. The forward optic 30 can be a sphero-cylindrical or aspheric lens or not, in various embodiments of the present disclosure. Also, the aft optic may not be a sphero-cylindrical or aspheric in various embodiments of the present disclosure.

Contraction refers to shortening of the radial distance between the axis 24 and the surfaces of the eye against which the base ends 42 and 84 rest as well as anterior movement of the plane of 42a and 60a relative to the optical nodal point of the eye. In the exemplary embodiment, in response to contraction of the ciliary muscle 18 for accommodation, the forward optic 30 moves anteriorly and the aft optic 40 can move posteriorly, anteriorly or remain stationary depending on stanchion design and pressure from the capsular bag. The stanchions 28 and 38 are sufficiently rigid to transmit movement, including converting movement toward the axis 24 by the ciliary muscle into movement of the optics 30, 40 along the axis 24.

Figure 3:
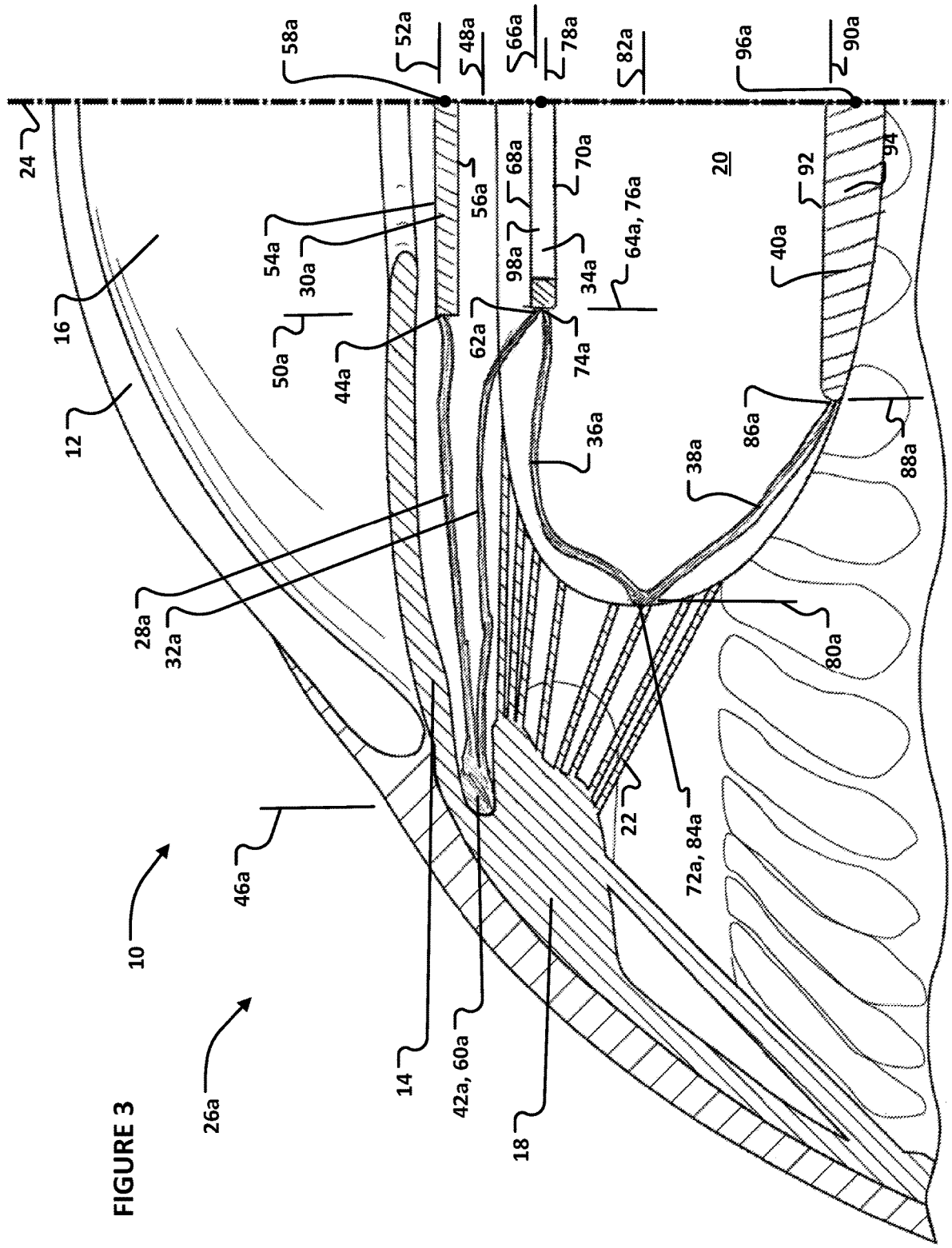
FIG. 3 is a cross-section of a second exemplary embodiment of the present disclosure positioned in an eye.

Referring now to FIG. 3, in another embodiment of the present disclosure, an accommodating intraocular lens assembly 26a can include a plurality of first stanchions 28a, a forward optic 30a, a plurality of second stanchions 32a, an intermediate member 34a, a plurality of third stanchions 36a, a plurality of fourth stanchions 38a, and an aft optic 40a. The plurality of first stanchions 28a can each extend between a respective first base end 42a and a respective first distal end 44a. The plurality of first base ends 42a can be disposed in spaced relation to one another about a first arcuate periphery 46a in a first plane 48a. The plurality of first distal ends 44a can be disposed in spaced relation to one another about a second arcuate periphery 50a in a second plane 52a. The first arcuate periphery 46a can have a greater radius than the second arcuate periphery 50a. The first arcuate periphery 46a and the second arcuate periphery 50a can be centered on the central optic axis 24. The first plane 48a and the second plane 52a can be spaced from one another along the central optic axis 24.

The forward optic 30a can have a first anterior side 54a and a first posterior side 56a and a first center 58a disposed between the first anterior side 54a and the first posterior side 56a. The forward optic 30a can be connected with each of the plurality of first distal ends 44a. The first center 58a of the forward optic 30a is moved along the central optic axis 24 in response to contraction of the first arcuate periphery 46a.

The plurality of second stanchions 32a can each extend between a respective second base end 60a and a respective second distal end 62a. The plurality of second base ends 60a can be disposed in spaced relation to one another about the first arcuate periphery 46a in the first plane 48a. The plurality of second distal ends 62a can be disposed in spaced relation to one another about a third arcuate periphery 64a in a third plane 66a. The first arcuate periphery 46a can have a greater radius than the third arcuate periphery 64a. The third arcuate periphery 64a can be centered on the central optic axis 24. In the exemplary embodiment, the radius of the third arcuate periphery 64a is substantially the same as the radius of the second arcuate periphery 50a. The second plane 52a and the third plane 66a can be spaced from one another along the central optic axis 24.

The intermediate member 34a can have an anterior side 68a and a posterior side 70a and can be connected with each of the plurality of second distal ends 62a. In the exemplary embodiment, the intermediate member 34a has a radially-outer perimeter that is circular is further defined as ring-shaped, with a body defining the radially-outer perimeter that is circular and an aperture 98a centered on the central optic axis 24. The plurality of third stanchions 36a can each extend between a respective third base end 72a and a respective third distal end 74a. The plurality of third base ends 72a can be disposed in spaced relation to one another about a fourth arcuate periphery 80a in a fourth plane 82a. The plurality of third distal ends 74a can be disposed in spaced relation to one another about a fifth arcuate periphery 76a in a fifth plane 78a. The plurality of third distal ends 74a can be connected to the intermediate member 34a. The fourth arcuate periphery 80a can have a greater radius than the fifth arcuate periphery 76a. The fourth arcuate periphery 80a and the fifth arcuate periphery 76a can be centered on the central optic axis 24. The second plane 52a and the fifth plane 78a can be spaced from one another along the central optic axis 24.

The plurality of fourth stanchions 38a can each extend between a respective fourth base end 84a and a respective fourth distal end 86a. The plurality of fourth base ends 84a can be disposed in spaced relation to one another about the fourth arcuate periphery 80a in the fourth plane 82a. The plurality of fourth distal ends 86a can be disposed in spaced relation to one another about a sixth arcuate periphery 88a in a sixth plane 90a. The fourth arcuate periphery 80a can have a greater radius than the sixth arcuate periphery 88a. The sixth arcuate periphery 88a can be centered on the central optic axis 24. The second plane 52a and the sixth plane 90a can be spaced from one another along the central optic axis 24.

The aft optic 40a can have a second anterior side 92a and a second posterior side 94a and a second center 96a disposed between the second anterior side 92a and the second posterior side 94a. The aft optic 40a can be connected with each of the plurality of fourth distal ends 86a whereby the second center 96a of the aft optic 40a is moved along the central optic axis 24 in response to contraction of the fourth arcuate periphery 80a.

Figure 4:
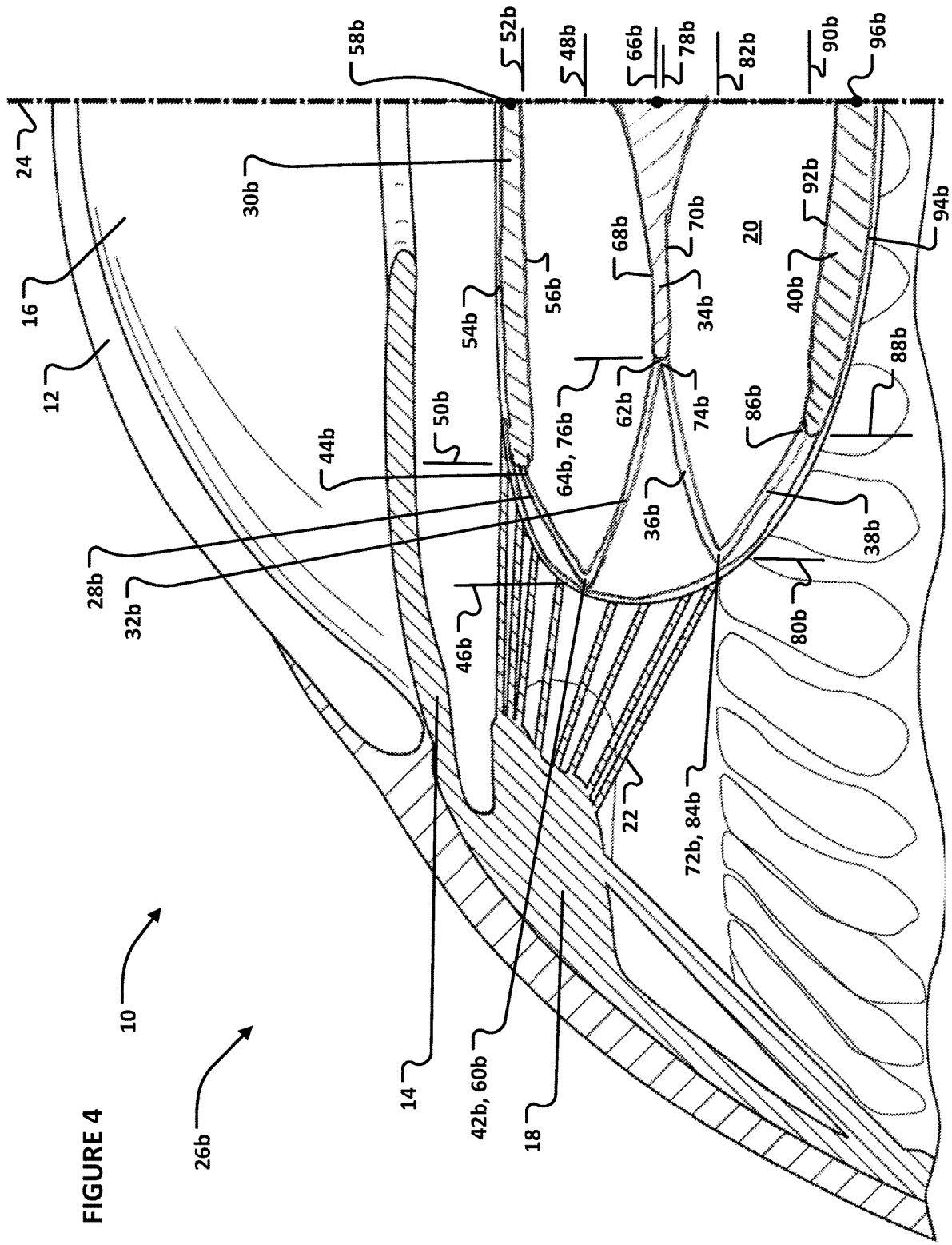
FIG. 4 is a cross-section of a third exemplary embodiment of the present disclosure positioned in an eye.

Referring now to FIG. 4, in another embodiment of the present disclosure, an accommodating intraocular lens assembly 26b can include a plurality of first stanchions 28b, a forward optic 30b, a plurality of second stanchions 32b, an intermediate member 34b, a plurality of third stanchions 36b, a plurality of fourth stanchions 38b, and an aft optic 40b. The plurality of first stanchions 28b can each extend between a respective first base end 42b and a respective first distal end 44b. The plurality of first base ends 42b can be disposed in spaced relation to one another about a first arcuate periphery 46b in a first plane 48b. The plurality of first distal ends 44b can be disposed in spaced relation to one another about a second arcuate periphery 50b in a second plane 52b. The first arcuate periphery 46b can have a greater radius than the second arcuate periphery 50b. The first arcuate periphery 46b and the second arcuate periphery 50b can be centered on the central optic axis 24. The first plane 48b and the second plane 52b can be spaced from one another along the central optic axis 24.

The forward optic 30b can have a first anterior side 54b and a first posterior side 56b and a first center 58b disposed between the first anterior side 54b and the first posterior side 56b. The forward optic 30b can be connected with each of the plurality of first distal ends 44b. The first center 58b of the forward optic 30b is moved along the central optic axis 24 in response to contraction of the first arcuate periphery 46b.

The plurality of second stanchions 32b can each extend between a respective second base end 60b and a respective second distal end 62b. The plurality of second base ends 60b can be disposed in spaced relation to one another about the first arcuate periphery 46b in the first plane 48b. The plurality of second distal ends 62b can be disposed in spaced relation to one another about a third arcuate periphery 64b in a third plane 66b. The first arcuate periphery 46b can have a greater radius than the third arcuate periphery 64b. The third arcuate periphery 64b can be centered on the central optic axis 24. The second plane 52b and the third plane 66b can be spaced from one another along the central optic axis 24.

The intermediate member 34b can have an anterior side 68b and a posterior side 70b and can be connected with each of the plurality of second distal ends 62b. The plurality of third stanchions 36b can each extend between a respective third base end 72b and a respective third distal end 74b. The plurality of third base ends 72b can be disposed in spaced relation to one another about a fourth arcuate periphery 80b in a fourth plane 82b. The plurality of third distal ends 74b can be disposed in spaced relation to one another about a fifth arcuate periphery 76b in a fifth plane 78b. The plurality of third distal ends 74b can be connected to the intermediate member 34b. The fourth arcuate periphery 80b can have a greater radius than the fifth arcuate periphery 76b. The fourth arcuate periphery 80b and the fifth arcuate periphery 76b can be centered on the central optic axis 24. The second plane 52b and the fifth plane 78b can be spaced from one another along the central optic axis 24.

The plurality of fourth stanchions 38b can each extend between a respective fourth base end 84b and a respective fourth distal end 86b. The plurality of fourth base ends 84b can be disposed in spaced relation to one another about the fourth arcuate periphery 80b in the fourth plane 82b. The plurality of fourth distal ends 86b can be disposed in spaced relation to one another about a sixth arcuate periphery 88b in a sixth plane 90b. The fourth arcuate periphery 80b can have a greater radius than the sixth arcuate periphery 88b. The sixth arcuate periphery 88b can be centered on the central optic axis 24. The second plane 52b and the sixth plane 90b can be spaced from one another along the central optic axis 24. The base ends 42b and 60b can be in the same plane or posterior to 72b and 84b in some embodiments The aft optic 40b can have a second anterior side 92b and a second posterior side 94b and a second center 96b disposed between the second anterior side 92b and the second posterior side 94b. The aft optic 40b can be connected with each of the plurality of fourth distal ends 86b whereby the second center 96b of the aft optic 40b is moved along the central optic axis 24 in response to contraction of the fourth arcuate periphery 80b.

Figure 5:
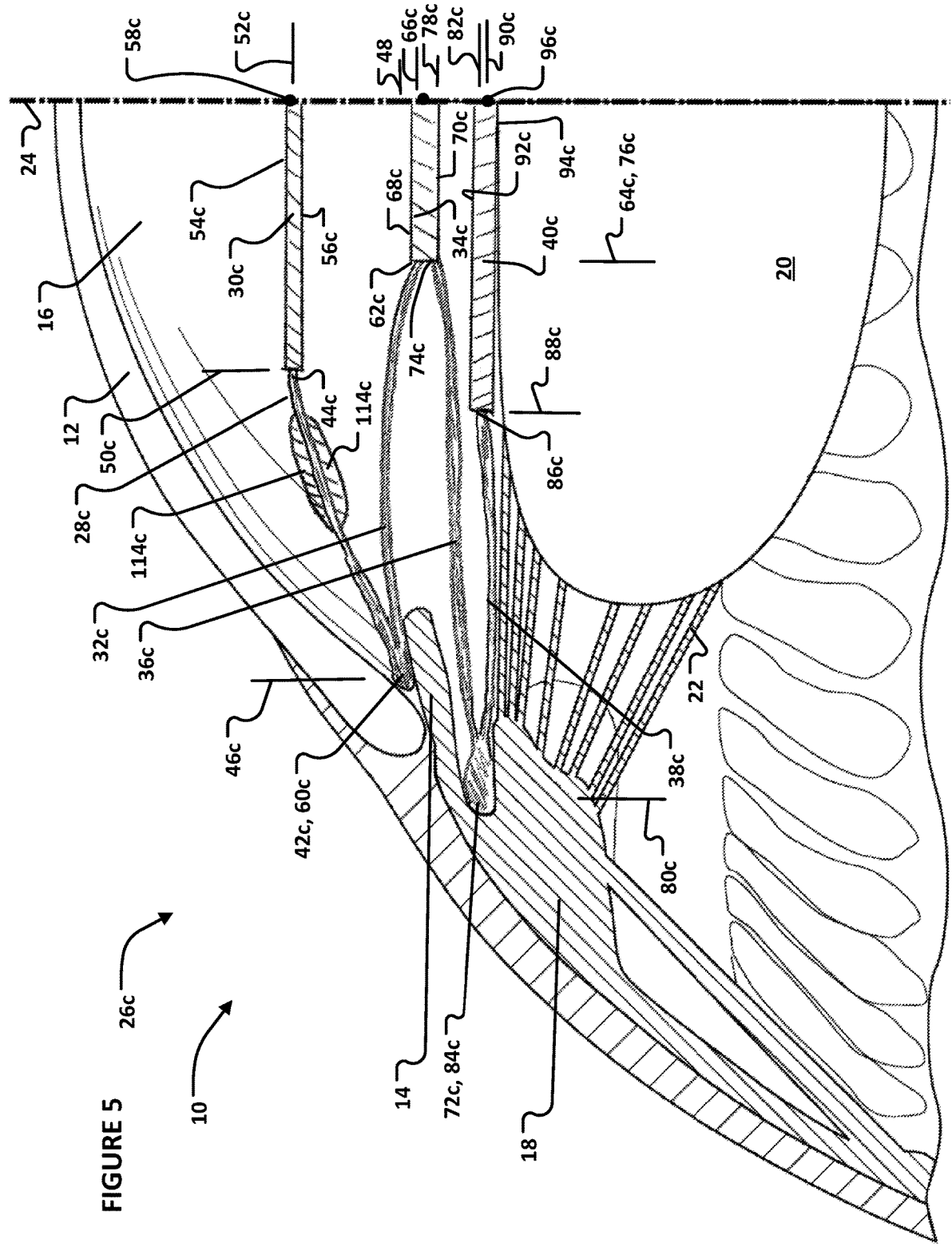
FIG. 5 is a cross-section of a fourth exemplary embodiment of the present disclosure positioned in an eye.

Referring now to FIG. 5, in another embodiment of the present disclosure, an accommodating intraocular lens assembly 26c can include a plurality of first stanchions 28c, a forward optic 30c, a plurality of second stanchions 32c, an intermediate member 34c, a plurality of third stanchions 36c, a plurality of fourth stanchions 38c, and an aft optic 40c. The plurality of first stanchions 28c can each extend between a respective first base end 42c and a respective first distal end 44c. The plurality of first base ends 42c can be disposed in spaced relation to one another about a first arcuate periphery 46c in a first plane 48c. The plurality of first distal ends 44c can be disposed in spaced relation to one another about a second arcuate periphery 50c in a second plane 52c. The first arcuate periphery 46c can have a greater radius than the second arcuate periphery 50c. The first arcuate periphery 46c and the second arcuate periphery 50c can be centered on the central optic axis 24. The first plane 48c and the second plane 52c can be spaced from one another along the central optic axis 24.

The forward optic 30c can have a first anterior side 54c and a first posterior side 56c and a first center 58c disposed between the first anterior side 54c and the first posterior side 56c. The forward optic 30c can be connected with each of the plurality of first distal ends 44c. The first center 58c of the forward optic 30c is moved along the central optic axis 24 in response to contraction of the first arcuate periphery 46c.

The plurality of second stanchions 32c can each extend between a respective second base end 60c and a respective second distal end 62c. The plurality of second base ends 60c can be disposed in spaced relation to one another about the first arcuate periphery 46c in the first plane 48c. The plurality of second distal ends 62c can be disposed in spaced relation to one another about a third arcuate periphery 64c in a third plane 66c. The first arcuate periphery 46c can have a greater radius than the third arcuate periphery 64c. The third arcuate periphery 64c can be centered on the central optic axis 24. The second plane 52c and the third plane 66c can be spaced from one another along the central optic axis 24.

The intermediate member 34c can have an anterior side 68c and a posterior side 70c and can be connected with each of the plurality of second distal ends 62c. The plurality of third stanchions 36c can each extend between a respective third base end 72c and a respective third distal end 74c. The plurality of third base ends 72c can be disposed in spaced relation to one another about a fourth arcuate periphery 80c in a fourth plane 82c. The plurality of third distal ends 74c can be disposed in spaced relation to one another about a fifth arcuate periphery 76c in a fifth plane 78c. The plurality of third distal ends 74c can be connected to the intermediate member 34c. The fourth arcuate periphery 80c can have a greater radius than the fifth arcuate periphery 76c. The fourth arcuate periphery 80c and the fifth arcuate periphery 76c can be centered on the central optic axis 24. The second plane 52c and the fifth plane 78c can be spaced from one another along the central optic axis 24.

The plurality of fourth stanchions 38c can each extend between a respective fourth base end 84c and a respective fourth distal end 86c. The plurality of fourth base ends 84c can be disposed in spaced relation to one another about the fourth arcuate periphery 80c in the fourth plane 82c. The plurality of fourth distal ends 86c can be disposed in spaced relation to one another about a sixth arcuate periphery 88c in a sixth plane 90c. The fourth arcuate periphery 80c can have a greater radius than the sixth arcuate periphery 88c. The sixth arcuate periphery 88c can be centered on the central optic axis 24. The second plane 52c and the sixth plane 90c can be spaced from one another along the central optic axis 24.

The aft optic 40c can have a second anterior side 92c and a second posterior side 94c and a second center 96c disposed between the second anterior side 92c and the second posterior side 94c. The aft optic 40c can be connected with each of the plurality of fourth distal ends 86c whereby the second center 96c of the aft optic 40c is moved along the central optic axis 24 in response to contraction of the fourth arcuate periphery 80c.

Figure 6:
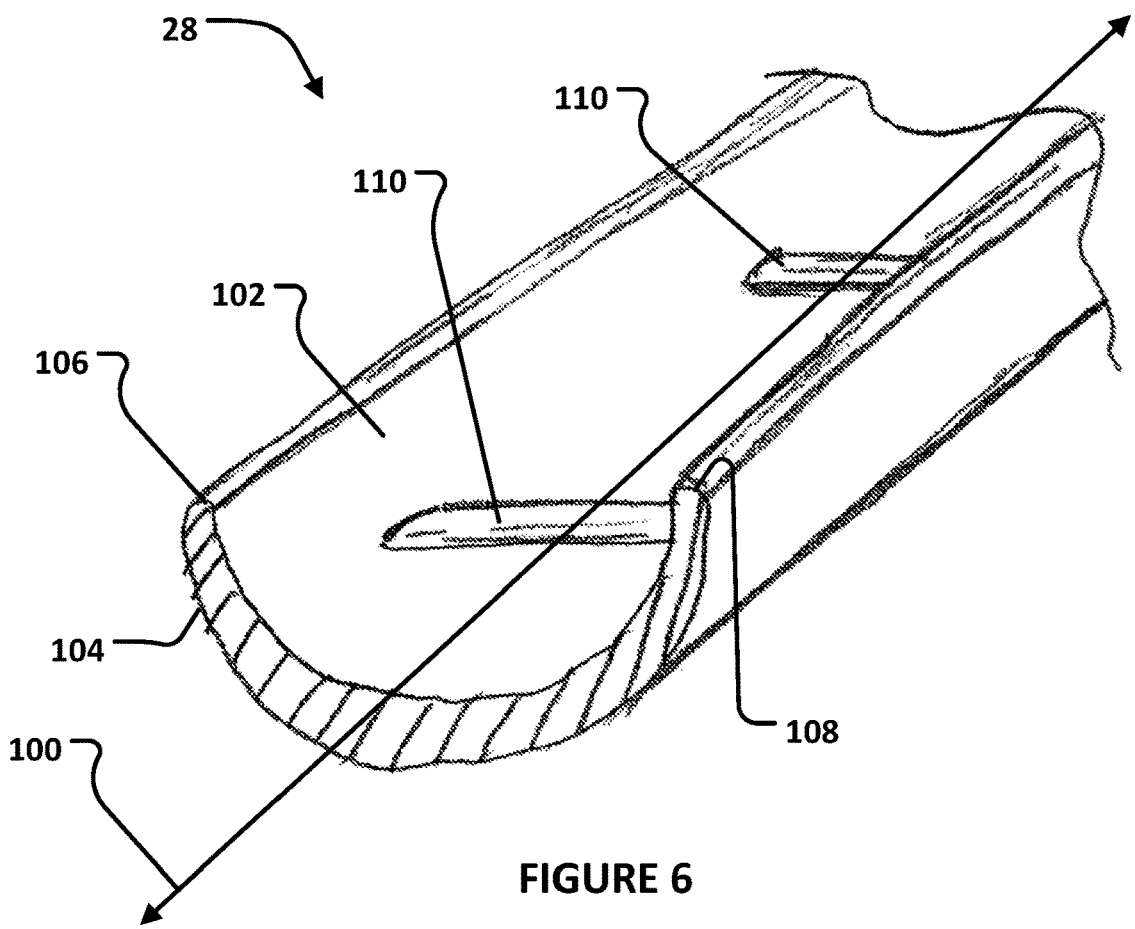
FIG. 6 is a perspective view of an exemplary stanchion of the present disclosure.

Any one or more of the first stanchions 28, 28a, 28b, 28c, the second stanchions 32, 32a, 32b, 32c, the third stanchions 36, 36a, 36b, 36c, and/or the fourth stanchions 38, 38a, 38b, 38c can define a cross-section of any shape, such as a circle, triangle, quadrilateral, ellipse, or some other shape. An accommodating intraocular lens assembly according to any of the embodiments 26, 26a, 26b, 26c can include one or more stanchions having a cross-section as shown in FIG. 6. Any one or more of the first stanchions 28, 28a, 28b, 28c, the second stanchions 32, 32a, 32b, 32c, the third stanchions 36, 36a, 36b, 36c, and/or the fourth stanchions 38, 38a, 38b, 38c can define a cross-section as shown in FIG. 6. An exemplary stanchion 28 defines a cross-section that is generally U or C shaped. The view shown in FIG. 6 is isometric or perspective and includes a view of the cross-section. The cross-section shown is taken in a plane that is normal to a central longitudinal axis 100 of the stanchion 28. The base end of the stanchion 28 is positioned at one end of the axis 100 and the distal end of the stanchion is positioned at the opposite end of the axis 100. It is noted that the axis 100 and the stanchion 28 are shown as straight in FIG. 6, but could be curved or partially-straight and partially-curved in various embodiments of the present disclosure. The cross-section is crescent-shaped with an inner arcuate surface 102 and an outer arcuate surface 104 extending between a first tip 106 and a second tip 108.

The stanchion 28 further comprises a plurality of bands 110. The bands 110 can be disposed in spaced relation to one another along the central longitudinal axis 100 of the stanchion 28. Each of the exemplary bands 110 interconnect respective first and second positions on the inner arcuate surface 102. The exemplary bands 110 can allow the stanchion 28 to retain a tighter U or C shape. The tighter the U or C shape, the more rigid the stanchion 28. In operation, when the accommodating intraocular lens including the stanchion 28 is positioned in an eye, a laser can be used to break one or more of the bands 110 to further open the U or C shape and thereby change the rigidity of the stanchion 28. This can be desirable to adjust the extent of movement of the optics 30 and/or 40 in response an extent of contraction of the ciliary muscle in the eye.

Figure 7:
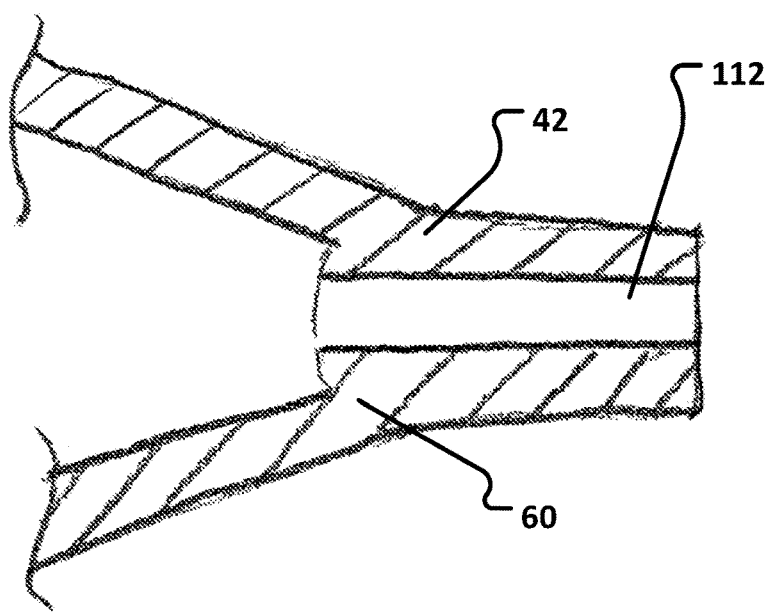
FIG. 7 is a cross-section through a pair of exemplary base ends of the present disclosure.

FIG. 7 is another feature that can be incorporated in any of the embodiments. In FIG. 7, a first base end 42 is interconnected to a second base end 60. An aperture 112 extends through the interconnected first base end 42 and second base end 60. The interconnected first base end 42 and second base end 60 can then function as stent for insertion in the supraciliary space, uveo-scleral pathway or the Trabecular meshwork. During insertion in the eye, the interconnected first base end 42 and second base end 60 can be driven into the Trabecular meshwork to function as a conduit to Schlemm's canal, or be anchored in the supraciliary space to provide an enhanced outflow channel for aqueous humor.

Figure 8:
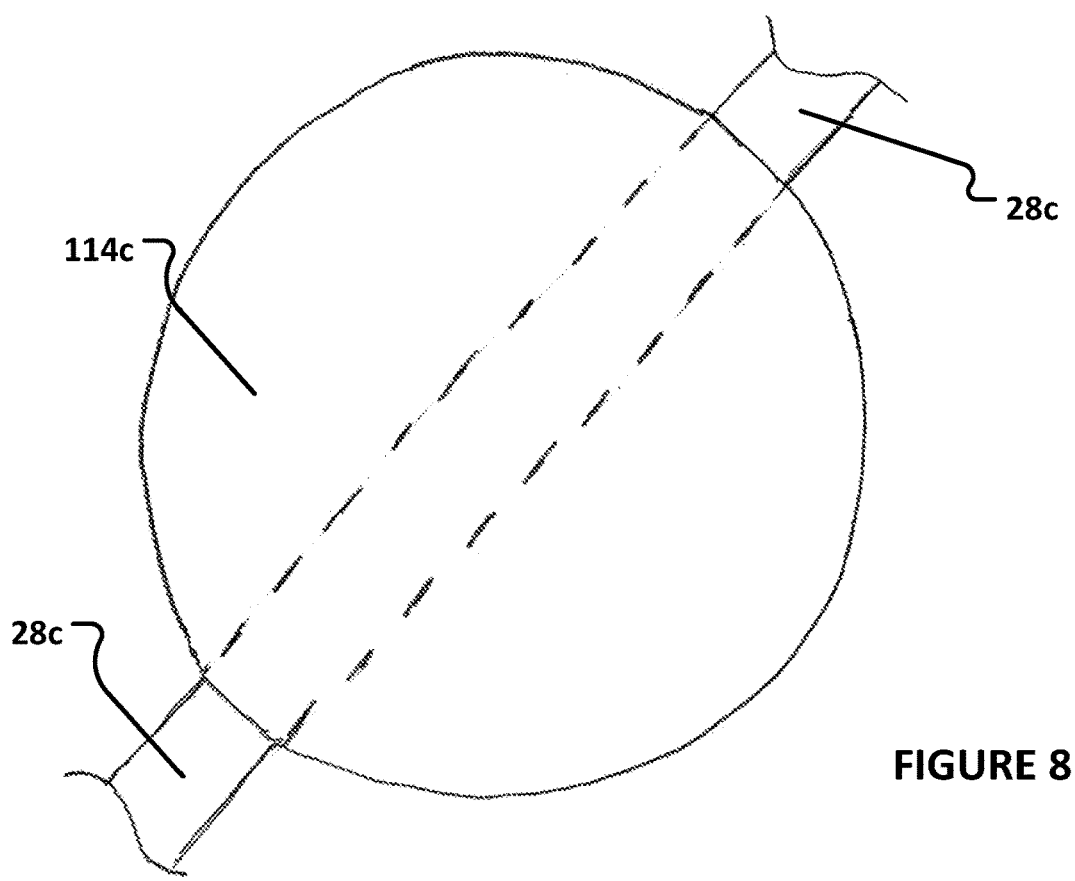
FIG. 8 is a view of an exemplary stanchion of the present disclosure.

FIG. 8 is a front view, similar in perspective to FIG. 2. FIG. 8 discloses a front view of a stanchion 28c of the embodiment shown in FIG. 5. An exemplary canopy 114c is positioned on and projecting away from opposite lateral sides of the stanchion 28c. The canopy can be incorporated in any of the embodiments. The exemplary canopy 114c is circular, but could be shaped differently. As shown in FIG. 5, the exemplary canopy 114c also projects away from the top and bottom sides of the stanchion 28c. The canopy 114c can be opaque and can be desirable for patients with Aniridia or iris damage. A canopy 114c can be positioned on each stanchion 28c. The canopy 114c can be sized so that the canopies 114c positioned on each stanchion 28c overlap.

Figure 9:
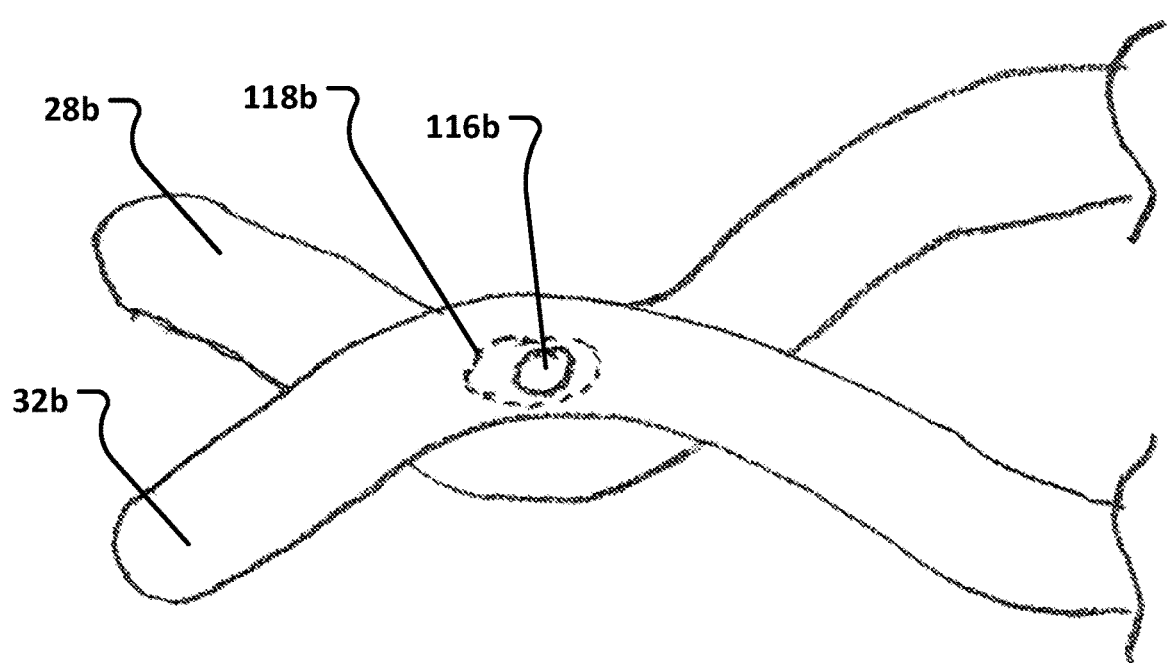
FIG. 9 is a side view of a pair of exemplary base ends of the present disclosure.

FIG. 9 is another feature that can be incorporated in any of the embodiments. A hinge pin 116b extends through apertures in two stanchions 28b, 32b. Any two stanchions can be interconnected through a hinge pin in various embodiments of the present disclosure. The hinge pin 116b is rotatable within the apertures defined by the stanchions 28b, 32b about a rotation axis. In one or more embodiments of the present disclosure, the aperture in one or both of the stanchions can be an elongated slot, such as referenced at 118b. In the elongated slot 118c, the hinge pin 116b would be rectilinearly moveable such that the rotation axis is laterally shiftable.

Figure 10:
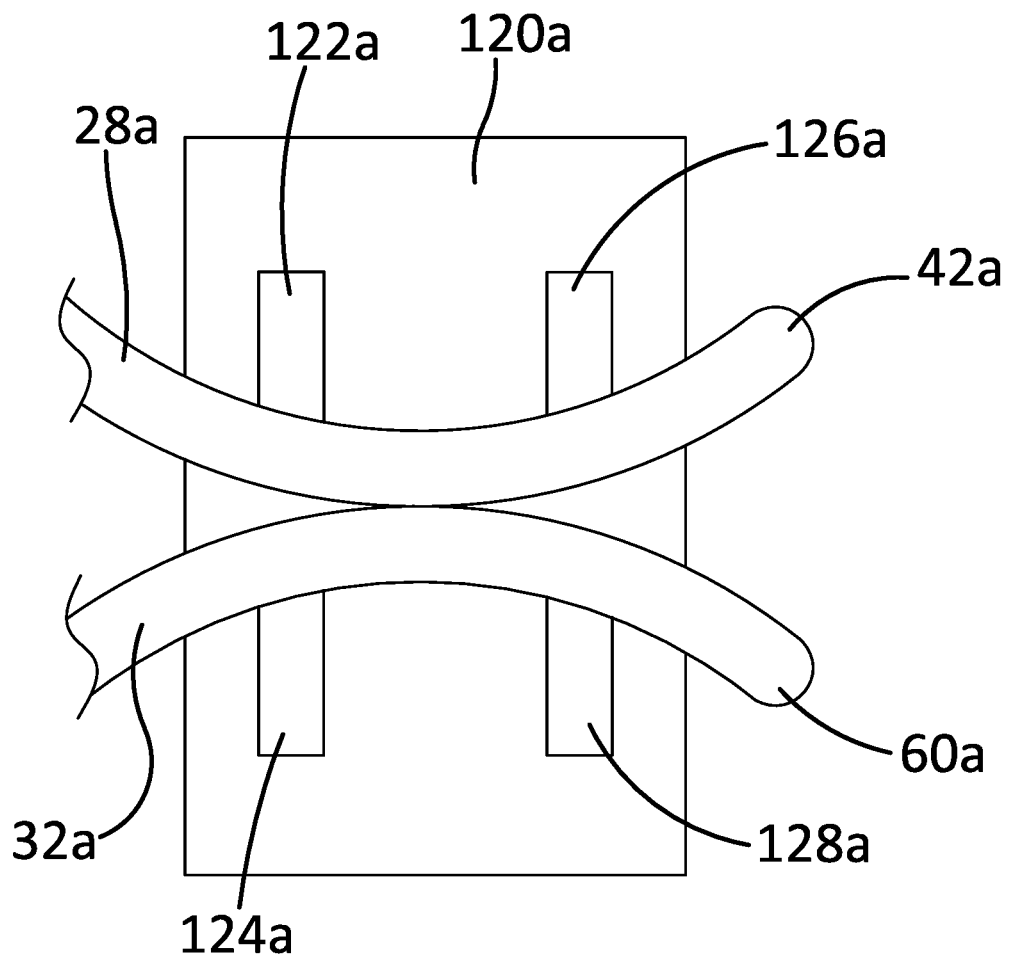
FIG. 10 is a side view of a collar and a pair of exemplary base ends of the present disclosure.

FIG. 10 is another feature that can be incorporated in any of the embodiments. An exemplary collar 120a at least partially surrounds two stanchions 28a, 32a at the base ends 42a, 60a. A first block 122a of material is positioned in the collar 120a and is adjacent to the stanchion 28a. The first block 122a contacts the stanchion 28a a first distance from the base end 42a. The first block 122a of material is configured to expand in response to the application of energy with a laser.

A second block 124a of material is positioned in the collar 120a adjacent to the stanchion 32a a second distance from the base end 60a. The second block 124a of material is also configured to expand in response to the application of energy with a laser. The second block 124a and the first block 122a are aligned with one another.

A third block 126a of material is positioned in the collar 120a and is adjacent to the stanchion 28a. The third block 126a contacts the stanchion 28a a third distance from the base end 42a. The third block 126a of material is configured to expand in response to the application of energy with a laser. The third distance less than the first distance, so the third block 126a is closer to the base end 42a than the first block 122a.

A fourth block 128a of material is positioned in the collar 120a adjacent to the stanchion 32a a fourth distance from the base end 60a. The fourth block 128a of material is also configured to expand in response to the application of energy with a laser. The fourth block 128a and the third block 126a are aligned with one another. The fourth distance less than the second distance, so the fourth block 126a is closer to the base end 60a than the second block 124a.

In operation, when the accommodating intraocular lens including the collar 120a is positioned in an eye, a laser can be applied to any one of the blocks 124a-128a to expand that block and urge the adjacent stanchion 28a or 32a up or down (based on the perspective of FIG. 10). This can be desirable to adjust how that stanchion transmits motion generated by muscles of the eye to motion of the optic 30.

In a method of using any embodiment of the accommodating intraocular lens assembly, the intermediate ring member can be wound relative to the forward and aft optics about the central optic axis 24. For example, the ring member can be rotated clockwise and the forward and aft optics restrained from rotation. This will draw the stanchions in between the forward optic and the aft optic, as well as draw the optics together. After the winding, the accommodating intraocular lens assembly can be folded in half, like a taco shell, while retaining the stanchions in between the forward optic and the aft optic. The wound and folded lens assembly can then be inserted into the eye, such as through a slit formed in the cornea. When the lens is positioned in the eye, the forward optic and the aft optic can be positioned against respective surfaces defined by the eye. The lens can then be released to unwind. The intermediate member can spin while both of the forward optic and aft optic remain relatively substantially stationary. For example, the neither the forward or aft optic will rotate less then three hundred and sixty degrees, or less than one hundred and eighty degrees, or less than ninety degrees, or less than twenty degrees, or zero degrees in one or more exemplary embodiments of the present disclosure. This prevents damage to the surfaces within the eye that abut the optics.

Embodiments of the present disclosure can be positioned in a plurality of different orientations within the eye. In FIG. 1, the optics 30 and 40 are on opposite sides of the iris 14. The forward optic 30 is positioned facing the anterior side of the iris 14 and the aft optic 40 is positioned facing the posterior side of the iris 14. In FIG. 3, the forward optic 30a is positioned facing the posterior side of the iris 14 of the eye but outside of the capsular bag 20 while the aft optic 40a is positioned in the capsular bag 20. In FIG. 4, the forward optic 30b, the intermediate member 34b, and the aft optic 40b are positioned in the capsular bag 20 of the eye.

One or more embodiments of the present disclosure can provide a Haptic design that maintains stability of its Haptic Passenger in the ciliary sulcus during ocular movement due to its shape and size. The haptic can be composed of stanchions which attach to the circumference of a fixed ring member at one end, and whose other ends describe a circular oval that forms a variable "virtual ring." The planar separation of the fixed ring member and the virtual ring can be dependent on the angles formed by the stanchions relative to the rings, while their lengths can remain essentially constant.

One or more embodiments of the present disclosure can prevent dislocation by gravity, inertia and flow of intraocular fluids, and mechanical forces exerted by adjacent intraocular structures both static and dynamic. The stability can be achieved by the size, shape, and/or composition of the haptic arrangement with the size being selected on the basis of pre-operative measurements made on each patient. The components that define the virtual ring (delineated by base end of stanchions) can be arranged so that they form a an oval circle of a variable diameter whose maximum extent corresponds to that of the ciliary sulcus (SSD) when CBA is relaxed and whose minimum extent corresponds to the diameter of the ciliary sulcus (SSD) when CBA is maximally activated. The said diameter can be oval shaped rather than strictly circular, to conform to the shape of the human ciliary sulcus.

The virtual ring of contact elements (base end of stanchions) can be made of a size and shape that fit securely into the ends of the ciliary sulcus without slippage or biological damage. The material can be bio-compatible and deformable but have sufficient structural memory to be folded prior to insertion into the eye through a small corneal incision and then unfolded into position within the ciliary sulcus of the eye.

The haptic design can thus be suited by dimensions and material of composition for stable and accurate surgical placement in the ciliary sulcus of the human eye between the anterior face of the lens capsule and zonules, and the posterior surface of the iris. A first anatomical change caused by CBA can be utilized by one or more embodiments of the present disclosure as shape-changing mechanisms is the decrease in diameter of the ciliary sulcus (perpendicular to the visual axis) due to annular contraction. This is measured as a decrease in the sulcus to sulcus diameter (SSD) which causes the virtual ring to contract, increasing separation of between fixed and virtual rings and so moving the fixed ring member and haptic passenger forward towards the cornea relative to the plane of the SSD circle. A second anatomical change can be anterior movement of the ciliary sulcus due to CB contraction. This causes forward movement of the plane of the SSD circle relative to the fixed points of the ocular globe caused by ciliary muscle contraction, resulting in forward movement of the virtual ring towards the cornea, which is additive in effect to the forward movement of the fixed ring member caused by reduction in SSD. A third anatomical change can be anterio-posterior pressure or compression at the ciliary sulcus between the zonules and the posterior surface of the iris due to forward movement of the ciliary body. Anterio-posterior pinching occurring in the ciliary sulcus due to annular contraction of the ciliary muscle results in increased compression at the ciliary sulcus from anatomical "crowding" against the posterior surface of the iris.

Ciliary sulcus placement effectively harnesses the three main functional elements of the ciliary muscle (longitudinal, oblique and annular) which on ciliary muscle contraction generate mechanical force that is matched to movements of single or multiple optic IOLS. Ciliary body contraction forces can be thus used to convert contraction to anterior displacement of the ring member of fixed circumference offset from the plane of the contracting circle. Embodiments of the present disclosure may be single or double (dual optic), convert contraction to move pins or pistons relative to a tangential bar or ring, and squeeze fluid. This allows a single or dual optic design in the configuration whereby equatorial reduction in circumference of an approximately circular anatomical trench associated with the ciliary muscle allows purchase on multiple contact points causing a corresponding reduction in circumference of the circle joining the contact points so that the contact pints contract in relation to each other without the need for sliding relative to the circular anatomical trench. The contact points serving as hinges whose relative movement is translated into variation of optical power to allow for close focusing on objects when accommodation is voluntarily initiated by contraction of the ciliary muscle. The movement described can be either increased separation of multiple optics of the IOL or forward movement of the center of a single optic.

One or more embodiments of the present disclosure can provide a Haptic design that is well suited for safe insertion through a small incision by being composed of multiple spoke like flexible elements arranged in a radial fashion connecting at least one fixed ring member to a virtual ring.

Other benefits of the present disclosure include efficient mechanical linkage with ciliary body contraction whether placed in capsular bag or ciliary sulcus. Multiple, flexible interconnected struts provide error correction for asymmetry and minor mis-positioning as well as some redundancy in case of damage during insertion. Small bulk allows for easy folding for insertion. Further, the performance does not depend on integrity of capsular bag (or zonules when placed in sulcus).

One or more embodiments of the present disclosure can provide a Haptic design that moves in harmony with internal ocular structures. The haptic flexes, contracts, expands and changes shape in a reversible manner in response to, and while in apposition with dynamic intraocular structures such as annular muscles, elastic capsules, supporting fibers and ocular connective tissue without presenting mechanical resistance that may damage ocular structures during such repeated and reversible mechanical changes.

A desirable aspect of one or more embodiments of the present disclosure can be point-to-point contraction linking (PPCL) in which the contact points are multiple enough to distribute force and support, spaced horizontally, vertically and all other important intermediate meridians, and large enough to provide support and make contact without damage but small enough and/or curved to offer minimal resistance to and friction against elastic dynamically contracting intra-ocular structures such as annular muscles or elastic capsules.

One or more embodiments of the present disclosure can provide a Haptic design whose cyclic movements in response to internal ocular structures can be used to predictably alter the force, tension and spatial separation between its constituent elements.

One or more embodiments of the present disclosure can provide a Haptic design composed of elements that are rigid and connected at certain points but flexible and elastically jointed at others so that may move in relation to one another and the eye but maintain stable fixation overall once implanted in the eye.

One or more embodiments of the present disclosure can provide a Haptic design that compresses in response to CB contraction in a predictable manner without significantly impeding CB contraction by virtue of point-to-point deformability. By thus compressing in response to CB contraction, one or more embodiments of the present disclosure can provide a Haptic design that links anatomical changes occurring during CBA, to variations in mechanical forces between the elements of the haptic. By virtue of the variation of force, tension and spacing between the elements of the rigid but elastically jointed haptics applies forces on the Haptic Passenger.

One or more embodiments of the present disclosure can provide a Haptic design in which the cyclic variations of force, tension and separation between its constituent elements can be linked to predictable variations in the properties of the Haptic Passenger. In the specific case where the Haptic Passenger is an optical lens system or "optic," the power of the optic can be reversibly and predictably varied through various mechanisms depending on the design of the lens system.

One or more embodiments of the present disclosure can provide a Haptic design which when manufactured to the appropriate dimensions is well suited for placement within the capsular bag of the eye. One or more embodiments of the present disclosure can provide a Haptic design allowing for attachment of the Haptic Passenger after the Haptic has been implanted in the eye so that the Haptic can be placed within the eye before the insertion of the Haptic Passenger. One or more embodiments of the present disclosure can provide a Haptic design that when placed prior to capsule rhexis provides stability and support of the lens capsule, which facilitates the performance of surgery. One or more embodiments of the present disclosure can provide a Haptic design that when placed prior to capsule rhexis can be adapted to improve pupillary dilation and thus facilitates the performance of surgery.

For desirable placement and harnessing of the ciliary body power, it may be desirable to have a two component IOL system in which the haptic passenger (a single or dual optic IOL) is attached within the eye to a ring-shaped haptic. Thus, either the forward or aft optic in the exemplary embodiments would be attached within the eye to an "outer" ring-shaped haptic, wherein a ring member in the middle would be an intermediate ring member. The haptic itself is circular flat disc open in the center which can be implanted in the ciliary sulcus after an incision is made but before the anterior capsule is opened (capsulorhexis, or simply rhexis). This ring would confer some additional benefits in performance of the surgery such as maintaining AC depth and preventing rapid fluctuations to protect zonules, holding anterior capsule taught to improve capsulorhexis, providing a potential platform for (detachable) iris hooks or iris lip to improve pupillary dilation, providing a secure anchor linked to the ciliary sulcus against which optic/haptic complex can be placed to transmit kinetic force of ciliary muscle contraction and convert it to optical changes in IOL power, and providing a ring member for potential post-operative mechanical/optical property modification by selective application of laser energy.

One or more embodiments of the present disclosure can provide a haptic that can be implanted separately from the haptic passenger, which has the advantage that it can be placed within the eye without the optic (or other haptic passenger). If the haptic passenger does not present an obstruction to surgery (such as that presented by a centrally located optic), it may be implanted at an earlier stage of surgery and thus facilitate subsequent steps of the surgical procedure. The modular IOL allows a two stage implantation. A first benefit of the two stage implantation are that it allows the haptic to be securely placed and seated in the ciliary sulcus before further surgical steps distort the anatomy around the ciliary sulcus. A haptic unfolded behind the iris is almost certain to become located in the ciliary sulcus because its posterior migration is limited by the anterior surface of a lens. It cannot pass beyond the anterior capsule, as the anterior capsule of the lens is still intact at this stage of the surgery. A second benefit is that the haptic can incorporated benefits of other surgical devices without the separate need for these devices, such as pupil expanders and anterior chamber stabilizing rings.

Design considerations for haptic in modular (two stage) IOL system include the area of touch wherein the slant of ring member and curve of the stanchions can be optimized by mathematical modeling to enhance refractive change per unit of ciliary muscle contraction, optic configurations such as can use single, dual or multiple optic configurations to simulate accommodation, allowing the ring member to have a gap (open or horseshoe shape) to allow for easier introduction past iris and assist with iris displacement or be a continuous circle, the inside edge can have a groove to accommodate optic, and the optic can have lip to fix against ring member at one end and two other lips or snaps to fix into place.

One or more embodiments of the present disclosure can provide a Haptic design that occupies and stretches the area adjacent to the ciliary body of the eye in a manner that may increase aqueous humor outflow and treat glaucoma following surgery. This is a novel concept and does not rely on a modular, two stage IOL (or any of the other elements of the ring member design other than ciliary sulcus placement) but on the design of the stanchion elements and interconnecting bands/rings so that they cause stretching and tension at a specific point near the base of the iris to open the aqueous humor drainage channels of the eye. The goal is to mimic an effect of certain glaucoma medicines that achieve the same result by causing contraction of the ciliary muscle. Perfection of this embodiment will require description of the optimum design of the base end of the haptics that sit in the sulcus, and perhaps other embellishments so it may best to allude to it in case details distract from the AIOL functioning.

One or more embodiments of the present disclosure can provide a Haptic design that allows for post-operative adjustment of amplitude of IOLA by selective application of energy to its elements to alter their elasticity, tension, relative separation placement within the eye.

One or more embodiments of the present disclosure can provide a Haptic design that allows for post-operative adjustment of lens spherical and or toric power by selective application of energy to its elements to alter their elasticity, tension, relative separation placement within the eye. Embellishments made possible by selective application of energy to the haptics through dilated pupils include the ability to modify spherical power, the ability to modify toric power, and the ability to modify asphericity.

An optic design (either as a single optic design or one or both of a dual optic design) which can be incorporated into a single stage or modular IOL system and which can be part of an AIOL or conventional IOL in which the Haptic Passenger is an optic in the form of a flexible lens system having a periphery containing components that can expand or contract in response to selective application of energy, whose expansion and contraction alters the central curvature and thickness of the lens. Embellishments made possible by selective application of energy at the periphery of at least one of the optics through dilated pupils include the selective application of energy at the optic periphery can alter the optical properties of the lens optic by increasing the pinching action of rivet type supports connecting the anterior and posterior surfaces of an optic, separated by a viscolelastic fluid. This arrangement allowing post-operative treatment that allows modification of the following lens optical properties: spherical power, cylindrical (Toric) power and axis to correct astigmatism, and correction of irregular astigmatism and higher order optical aberrations.

There are a number of stanchion contact designs used to translate the mechanical forces generated by CBA into IOLA by enhancing optic movement contemplated by the present disclosure including various contact designs, rigidity changes and curvatures.

One or more embodiments of the present disclosure can provide a Haptic design that by virtue of allowing later attachment of the Haptic Passenger also allows for its own injection into the eye in the form of a helical strip. The flexible strip may be inserted into the eye using an instrument or injector and once injected into the eye forms a closed circular ring, forms a "C" shaped ring, or forms a "C" shaped ring whose ends can be joined to form a closed circular ring.

One or more embodiments of the present disclosure can provide a Haptic design that by virtue of allowing later attachment of the Haptic Passenger also allows for its own insertion into the eye through a small incision in the form of a circle with at least four points of elastic articulation. This method of articulating the relatively rigid segments of the circle allows the Haptic to fit through a narrow incision whilst maintaining enough rigidity to be guided behind the iris and preventing excessive disruption of the space between the iris and the lens capsule.

Because of the anatomy of the ocular globe, a small corneal incision, if constructed in a step like fashion at the correct location with a special instrument, can be self-sealing so that the pressure of fluid within the eye will keep it closed until it heals. The upper limit to the length of such an incision is generally considered to be no more than about three millimeters. It can be desirable that an IOL optic be at least about five millimeters in diameter to focus light on the retina. A smaller optic could cause glare, reflections, and other troublesome symptoms. To span the diameter of the anterior chamber, capsular bag or ciliary sulcus and desirably suspend the optic in place, the distance between opposite ends of the haptics should be at least about nine millimeters Any device that requires stable placement in the sulcus or capsular bag will likely be subject to these constraints. Therefore, any IOL, however complex or elegant in design, will have extremely limited utility unless it can be placed within the eye through a small incision and also meet the minimum size requirements of the optic and haptic diameters. Several other anatomical and physiological factors place practical constraints on intraocular device design. Embodiments of the present disclosure can meet these practical constraints and provide patentable utility.

In various embodiments, the intended haptic passenger can be a multi-optic IOL that is one-piece or modular. Such embodiments can include a single ring member or more than one ring members. The rings of a one-piece or modular embodiment can be continuous. For one-piece embodiments, the mechanism of morphological change allowing for entry of the single ring member through small corneal incision can be limited by the incorporated IOL optic, which should be in the shape of a disc, plate or star that is folded. Fold configurations may be like a taco, roll, or concertina. Each fold method can use forceps or an injector cartridge. The enhanced mechanism for accurate stanchion placement once the embodiment is inside the eye can be a star-shaped profile of the haptic (a result of the ring member and stanchions), distinct rounded contact points defined by the base ends of the stanchions, with connections between the base ends presenting a rounded planar profile with intervening fenestrations to allow flexing of the haptic and the flow of intraocular fluids. The enhanced mechanism for accurate stanchion placement once the embodiment is inside the eye can also be an uncoiling motion, such as could occur in any the exemplary embodiments. The nature of the optics can be adjustable after surgery. Optic rotation during CBA would defeat some of the modification utility (especially astigmatism adjustment) unless the embodiment when uncoiled was configured to allow movement of the optics without rotation. The nature of the optics can be can be adjustable after surgery.

In some embodiments of the present disclosure, a plurality of stanchions can be interconnected with a ring member and the embodiment can omit a lens. Such an embodiment can be implanted in a patient's eye without a lens. Such an embodiment can be placed in the ciliary sulcus and thereby increase aqueous humor outflow by stretching open the trabecular meshwork. Such an embodiment, when placed in the ciliary sulcus, can also decrease aqueous humor production by ciliary body. Any of the structural embodiments of the present disclosure can be placed in the ciliary sulcus without a lens.

It is noted that one or more structures disclosed herein can be formed from ChronoFlex C®, attainable from Advan-Source Biomaterials Corp. of Wilmington, MA It is also noted that the display of any particular embodiment is not to be viewed as limiting. Embodiments can be sized to work within an empty capsular bag (after cataract extraction) when placed in the ciliary sulcus, anterior chamber, capsular bag, or a combination of these locations.

While the present disclosure has been described with reference to an exemplary embodiment, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the appended claims. The right to claim elements and/or sub-combinations that are disclosed herein is hereby unconditionally reserved. The use of the word "can" in this document is not an assertion that the subject preceding the word is unimportant or unnecessary or "not critical" relative to anything else in this document. The word "can" is used herein in a positive and affirming sense and no other motive should be presumed. More than one "invention" may be disclosed in the present disclosure; an "invention" is defined by the content of a patent claim and not by the content of a detailed description of an embodiment of an invention.

What is claimed is:
1. An intraocular optic assembly comprising:
   a plurality of first stanchions each extending between a respective first base end and a respective first distal end, said plurality of first base ends disposed in spaced relation to one another about a first arcuate periphery, said plurality of first distal ends disposed in spaced relation to one another about a second arcuate periphery, said first arcuate periphery having a greater radius than said second arcuate periphery;
   a first optic having a first anterior side and a first posterior side and a first center disposed between said first anterior side and said first posterior side, said first optic connected with each of said plurality of first distal ends whereby said first center of said first optic is moved along said central optic axis in response to contraction of said first arcuate periphery;
   a plurality of second stanchions each extending between a respective second base end and a respective second distal end, said plurality of second base ends disposed in spaced relation to one another about said first arcuate periphery, said plurality of second distal ends disposed in spaced relation to one another about a third arcuate periphery, said first arcuate periphery having a greater radius than said third arcuate periphery, said third arcuate periphery centered on said central optic axis;

an intermediate member having an anterior side and a posterior side and connected with each of said plurality of second distal ends;
a plurality of third stanchions each extending between a respective third base end and a respective third distal end, said plurality of third base ends disposed in spaced relation to one another about a fourth arcuate periphery, said plurality of third distal ends disposed in spaced relation to one another about a fifth arcuate periphery and connected to said intermediate member, said fourth arcuate periphery having a greater radius than said fifth arcuate periphery, said fourth arcuate periphery and said fifth arcuate periphery centered on said central optic axis;
a plurality of fourth stanchions each extending between a respective fourth base end and a respective fourth distal end, said plurality of fourth base ends disposed in spaced relation to one another about said fourth arcuate periphery, said plurality of fourth distal ends disposed in spaced relation to one another about a sixth arcuate periphery, said fourth arcuate periphery having a greater radius than said sixth arcuate periphery, said sixth arcuate periphery centered on said central optic axis;
an aft optic having a second anterior side and a second posterior side and a second center disposed between said second anterior side and said second posterior side, said aft optic connected with each of said plurality of fourth distal ends whereby said second center of said aft optic is moved along said central optic axis in response to contraction of said fourth arcuate periphery;
wherein said intermediate member is further defined as including at least one of a sphero-cylindrical lens, an aspheric lens, and a ring-shaped body defining a radially-outer perimeter that is circular and an aperture; and
wherein at least one of said plurality of first stanchions and said plurality of second stanchions and said plurality of third stanchions and said plurality of fourth stanchions further comprises a plurality of bands disposed in spaced relation to one another along a central longitudinal axis of said at least one stanchion, each of said exemplary bands interconnecting respective first and second positions on an inner arcuate surface of said at least one stanchion, said plurality of bands retaining said at least one stanchion in a C shape in cross-section.

2. An intraocular optic assembly comprising:
a plurality of first stanchions each extending between a respective first base end and a respective first distal end, said plurality of first base ends disposed in spaced relation to one another about a first arcuate periphery, said plurality of first distal ends disposed in spaced relation to one another about a second arcuate periphery, said first arcuate periphery having a greater radius than said second arcuate periphery;
a first optic having a first anterior side and a first posterior side and a first center disposed between said first anterior side and said first posterior side, said first optic connected with each of said plurality of first distal ends whereby said first center of said first optic is moved along said central optic axis in response to contraction of said first arcuate periphery;
a plurality of second stanchions each extending between a respective second base end and a respective second distal end, said plurality of second base ends disposed in spaced relation to one another about said first arcuate periphery, said plurality of second distal ends disposed in spaced relation to one another about a third arcuate periphery, said first arcuate periphery having a greater radius than said third arcuate periphery, said third arcuate periphery centered on said central optic axis;
an intermediate member having an anterior side and a posterior side and connected with each of said plurality of second distal ends;
a plurality of third stanchions each extending between a respective third base end and a respective third distal end, said plurality of third base ends disposed in spaced relation to one another about a fourth arcuate periphery, said plurality of third distal ends disposed in spaced relation to one another about a fifth arcuate periphery and connected to said intermediate member, said fourth arcuate periphery having a greater radius than said fifth arcuate periphery, said fourth arcuate periphery and said fifth arcuate periphery centered on said central optic axis;
a plurality of fourth stanchions each extending between a respective fourth base end and a respective fourth distal end, said plurality of fourth base ends disposed in spaced relation to one another about said fourth arcuate periphery, said plurality of fourth distal ends disposed in spaced relation to one another about a sixth arcuate periphery, said fourth arcuate periphery having a greater radius than said sixth arcuate periphery, said sixth arcuate periphery centered on said central optic axis;
an aft optic having a second anterior side and a second posterior side and a second center disposed between said second anterior side and said second posterior side, said aft optic connected with each of said plurality of fourth distal ends whereby said second center of said aft optic is moved along said central optic axis in response to contraction of said fourth arcuate periphery;
wherein said intermediate member is further defined as including at least one of a sphero-cylindrical lens, an aspheric lens, and a ring-shaped body defining a radially-outer perimeter that is circular and an aperture; and
wherein at least two of said plurality of first base ends and said plurality of second base ends and said plurality of third base ends and said plurality of fourth base ends, said at least two based ends interconnected and further comprises an aperture extending therethrough.

3. An intraocular optic assembly comprising:
a plurality of first stanchions each extending between a respective first base end and a respective first distal end, said plurality of first base ends disposed in spaced relation to one another about a first arcuate periphery, said plurality of first distal ends disposed in spaced relation to one another about a second arcuate periphery, said first arcuate periphery having a greater radius than said second arcuate periphery;
a first optic having a first anterior side and a first posterior side and a first center disposed between said first anterior side and said first posterior side, said first optic connected with each of said plurality of first distal ends whereby said first center of said first optic is moved along said central optic axis in response to contraction of said first arcuate periphery;
a plurality of second stanchions each extending between a respective second base end and a respective second distal end, said plurality of second base ends disposed in spaced relation to one another about said first arcuate periphery, said plurality of second distal ends disposed in spaced relation to one another about a third arcuate periphery, said first arcuate periphery having a greater radius than said third arcuate periphery, said third arcuate periphery centered on said central optic axis;

an intermediate member having an anterior side and a posterior side and connected with each of said plurality of second distal ends;

a plurality of third stanchions each extending between a respective third base end and a respective third distal end, said plurality of third base ends disposed in spaced relation to one another about a fourth arcuate periphery, said plurality of third distal ends disposed in spaced relation to one another about a fifth arcuate periphery and connected to said intermediate member, said fourth arcuate periphery having a greater radius than said fifth arcuate periphery, said fourth arcuate periphery and said fifth arcuate periphery centered on said central optic axis;

a plurality of fourth stanchions each extending between a respective fourth base end and a respective fourth distal end, said plurality of fourth base ends disposed in spaced relation to one another about said fourth arcuate periphery, said plurality of fourth distal ends disposed in spaced relation to one another about a sixth arcuate periphery, said fourth arcuate periphery having a greater radius than said sixth arcuate periphery, said sixth arcuate periphery centered on said central optic axis;

an aft optic having a second anterior side and a second posterior side and a second center disposed between said second anterior side and said second posterior side, said aft optic connected with each of said plurality of fourth distal ends whereby said second center of said aft optic is moved along said central optic axis in response to contraction of said fourth arcuate periphery;

wherein said intermediate member is further defined as including at least one of a sphero-cylindrical lens, an aspheric lens, and a ring-shaped body defining a radially-outer perimeter that is circular and an aperture; and wherein at least one of said plurality of first stanchions and said plurality of second stanchions and said plurality of third stanchions and said plurality of fourth stanchions further comprises a canopy projecting away from opposite lateral sides of said at least one of said plurality of first stanchions and said plurality of second stanchions and said plurality of third stanchions and said plurality of fourth stanchions, wherein said canopy is further defined as spaced from both said base end and said distal end of said at least one of said plurality of first stanchions and said plurality of second stanchions and said plurality of third stanchions and said plurality of fourth stanchions.

4. An intraocular optic assembly comprising:

a plurality of first stanchions each extending between a respective first base end and a respective first distal end, said plurality of first base ends disposed in spaced relation to one another about a first arcuate periphery, said plurality of first distal ends disposed in spaced relation to one another about a second arcuate periphery, said first arcuate periphery having a greater radius than said second arcuate periphery;

a first optic having a first anterior side and a first posterior side and a first center disposed between said first anterior side and said first posterior side, said first optic connected with each of said plurality of first distal ends whereby said first center of said first optic is moved along said central optic axis in response to contraction of said first arcuate periphery;

a plurality of second stanchions each extending between a respective second base end and a respective second distal end, said plurality of second base ends disposed in spaced relation to one another about said first arcuate periphery, said plurality of second distal ends disposed in spaced relation to one another about a third arcuate periphery, said first arcuate periphery having a greater radius than said third arcuate periphery, said third arcuate periphery centered on said central optic axis;

an intermediate member having an anterior side and a posterior side and connected with each of said plurality of second distal ends;

a plurality of third stanchions each extending between a respective third base end and a respective third distal end, said plurality of third base ends disposed in spaced relation to one another about a fourth arcuate periphery, said plurality of third distal ends disposed in spaced relation to one another about a fifth arcuate periphery and connected to said intermediate member, said fourth arcuate periphery having a greater radius than said fifth arcuate periphery, said fourth arcuate periphery and said fifth arcuate periphery centered on said central optic axis;

a plurality of fourth stanchions each extending between a respective fourth base end and a respective fourth distal end, said plurality of fourth base ends disposed in spaced relation to one another about said fourth arcuate periphery, said plurality of fourth distal ends disposed in spaced relation to one another about a sixth arcuate periphery, said fourth arcuate periphery having a greater radius than said sixth arcuate periphery, said sixth arcuate periphery centered on said central optic axis;

an aft optic having a second anterior side and a second posterior side and a second center disposed between said second anterior side and said second posterior side, said aft optic connected with each of said plurality of fourth distal ends whereby said second center of said aft optic is moved along said central optic axis in response to contraction of said fourth arcuate periphery;

wherein said intermediate member is further defined as including at least one of a sphero-cylindrical lens, an aspheric lens, and a ring-shaped body defining a radially-outer perimeter that is circular and an aperture; and a hinge pin extending through at least two of said plurality of first stanchions and said plurality of second stanchions and said plurality of third stanchions and said plurality of fourth stanchions.

5. An intraocular optic assembly comprising:

a plurality of first stanchions each extending between a respective first base end and a respective first distal end, said plurality of first base ends disposed in spaced relation to one another about a first arcuate periphery, said plurality of first distal ends disposed in spaced relation to one another about a second arcuate periphery, said first arcuate periphery having a greater radius than said second arcuate periphery;

a first optic having a first anterior side and a first posterior side and a first center disposed between said first anterior side and said first posterior side, said first optic connected with each of said plurality of first distal ends whereby said first center of said first optic is moved along said central optic axis in response to contraction of said first arcuate periphery;

a plurality of second stanchions each extending between a respective second base end and a respective second distal end, said plurality of second base ends disposed in spaced relation to one another about said first arcuate periphery, said plurality of second distal ends disposed in spaced relation to one another about a third arcuate periphery, said first arcuate periphery having a greater radius than said third arcuate periphery, said third arcuate periphery centered on said central optic axis;

an intermediate member having an anterior side and a posterior side and connected with each of said plurality of second distal ends;

a plurality of third stanchions each extending between a respective third base end and a respective third distal end, said plurality of third base ends disposed in spaced relation to one another about a fourth arcuate periphery, said plurality of third distal ends disposed in spaced relation to one another about a fifth arcuate periphery and connected to said intermediate member, said fourth arcuate periphery having a greater radius than said fifth arcuate periphery, said fourth arcuate periphery and said fifth arcuate periphery centered on said central optic axis;

a plurality of fourth stanchions each extending between a respective fourth base end and a respective fourth distal end, said plurality of fourth base ends disposed in spaced relation to one another about said fourth arcuate periphery, said plurality of fourth distal ends disposed in spaced relation to one another about a sixth arcuate periphery, said fourth arcuate periphery having a greater radius than said sixth arcuate periphery, said sixth arcuate periphery centered on said central optic axis;

an aft optic having a second anterior side and a second posterior side and a second center disposed between said second anterior side and said second posterior side, said aft optic connected with each of said plurality of fourth distal ends whereby said second center of said aft optic is moved along said central optic axis in response to contraction of said fourth arcuate periphery;

wherein said intermediate member is further defined as including at least one of a sphero-cylindrical lens, an aspheric lens, and a ring-shaped body defining a radially-outer perimeter that is circular and an aperture; and a collar at least partially surrounding at least two of said plurality of first stanchions and said plurality of second stanchions and said plurality of third stanchions and said plurality of fourth stanchions, said collar including at least one block of material adjacent to a first of said at least two of said plurality of first stanchions and said plurality of second stanchions and said plurality of third stanchions and said plurality of fourth stanchions and configured to expand in response to the application of energy with a laser.

* * * * *